US012006343B2

(12) United States Patent
Aran Perramon et al.

(10) Patent No.: US 12,006,343 B2
(45) Date of Patent: Jun. 11, 2024

(54) C4BP-BASED COMPOUNDS FOR TREATING IMMUNOLOGICAL DISEASES

(71) Applicant: FUNDACIO INSTITUT D'INVESTIGACIO BIOMEDICA DE BELLVITGE (IDIBELL), Barcelona (ES)

(72) Inventors: Josep M. Aran Perramon, Barcelona (ES); Luis Antonio Ruiz Avila, Barcelona (ES); Jordi Ortiz Sagrista, Barcelona (ES); Nuria Lluch Lafuente, Barcelona (ES)

(73) Assignee: FUNDACIO INSTITUT D'INVESTIGACIO BIOMEDICA DE BELLVITGE (IDIBELL), Barcelona (ES)

(*) Notice: Subject to any disclaimer, the term of this patent is extended or adjusted under 35 U.S.C. 154(b) by 0 days.

(21) Appl. No.: 16/603,427

(22) PCT Filed: Apr. 5, 2018

(86) PCT No.: PCT/EP2018/058773
§ 371 (c)(1),
(2) Date: Oct. 7, 2019

(87) PCT Pub. No.: WO2018/185244
PCT Pub. Date: Oct. 11, 2018

(65) Prior Publication Data

US 2020/0148731 A1 May 14, 2020

(30) Foreign Application Priority Data

Apr. 6, 2017 (EP) .................................... 17382187

(51) Int. Cl.

| | |
|---|---|
| ***A61K 38/13*** | (2006.01) |
| ***A61K 9/00*** | (2006.01) |
| ***A61K 45/06*** | (2006.01) |
| ***A61P 19/02*** | (2006.01) |
| ***A61P 37/06*** | (2006.01) |
| ***C07K 14/47*** | (2006.01) |

(52) U.S. Cl.
CPC ............ *C07K 14/472* (2013.01); *A61P 19/02* (2018.01); *A61P 37/06* (2018.01); *A61K 9/0019* (2013.01); *A61K 45/06* (2013.01)

(58) Field of Classification Search
CPC ................ A61K 2300/00; A61K 38/13; A61K 38/1725; A61K 38/1774; A61K 38/1793; A61K 38/2278; A61K 2039/54; A61K 2039/545; A61K 2039/57; A61K 45/06; A61K 9/0019; A61P 19/02; A61P 37/06; C07K 14/472
See application file for complete search history.

(56) References Cited

U.S. PATENT DOCUMENTS

| | | | | |
|---|---|---|---|---|
| 10,106,589 B2 | 10/2018 | Aran Perramon | | |
| 2004/0197316 A1* | 10/2004 | Tsokos .................... | A61P 37/00 424/93.21 |
| 2014/0271569 A1* | 9/2014 | Tang ...................... | A61K 35/28 424/93.7 |

FOREIGN PATENT DOCUMENTS

| | | | |
|---|---|---|---|
| WO | 2013/010998 A | 1/2013 | |
| WO | WO-2013010998 A2 * | 1/2013 | ............ A61K 35/15 |

OTHER PUBLICATIONS

Rheumatoid Arthritis from Merck Manual, pp. 1-20. Accessed Feb. 12, 2023. (Year: 2023).*
Human Immunodeficiency Virus Infection from Merck Manual, pp. 1-31. Accessed Feb. 12, 2023. (Year: 2023).*
Blom et al., "C4b-binding protein (C4BP) inhibits development of experimental arthritis in mice," Annals of the Rheumatic Diseases, 2009, 68(1): 136-142. Published online Feb. 14, 2008. (Year: 2008).*
Saini, et al., "Alloimmunity Induced Autoimmunity as a Potential Mechanism in The Pathogenesis of Chronic Rejection of Human Lung Allografts", J. Heart Lung Transplant. Jun. 2011; 30(6): 624-631.
Sanchez-Coral, "Isoforms of Human C4b-binding Protein", The Journal of Immunology, pp. 4030-4036, Downloaded from http://www.jimmunol.org/ at Univ de Barcelona Biblioteca on Dec. 10, 2019.
Seetharam, et al., "Alloimmunity and autoimmunity in chronic rejection", Curr Opin Organ Tansplant, Aug. 2010; 15(4): 531-536.
Shalapour, et al., "Immunity, inflammation, and cancer: an eternal fight between good and evil", The Journal of Clinical Investigation, vol. 125, No. 9, Sep. 2015, pp. 3347-3355.
Steinman, et al., "Tolerogenic Dendritic Cells", Annu. Rev. Immunol. 2003 21:685-711.
Teichmann, et al., "Dendritic Cells in Lupus are not Required for Activation of T and B Cells but Promote their Expansion Resulting in Tissue Damage", Immunity, Dec. 14, 2010; 33(6): 967-978.
Thompson, et al., "Clustal W: improving the sensitivity of progressive multiple sequence alignment through sequence weighting, position-specific gap penalties and weight matrix choice", Nucleic Acids Research, 1994, vol. 22, No. 22, 4673-4680.
Urowitz, et al., "Evolution of Disease Burden Over Five Years in a Multicenter Inception Systemic Lupus Erythematosus Cohort", Arthritis Care & Research, vol. 64, No. 1, Jan. 2012, pp. 132-137.

(Continued)

*Primary Examiner* — Julie Ha
(74) *Attorney, Agent, or Firm* — Kramer & Amado, P.C.

(57) ABSTRACT

Compounds for use in the prevention and/or treatment of immunological diseases, particularly rheumatoid arthritis, systemic lupus erythematosus and lupus nephritis, are described, characterized by the subcutaneous administration of isoforms of C4BP lacking the beta chain or polypeptides comprising the CCP6 region of the alpha chain of C4BP no more than once a week or at a dose ranging from 0.24 $mg/m^2$ to 9.99 $mg/m^2$. Pharmaceutical compositions comprising from 0.45 mg to 18.90 mg of these compounds for the prevention and/or treatment of these diseases are also described.

15 Claims, 8 Drawing Sheets

Specification includes a Sequence Listing.

(56) References Cited

OTHER PUBLICATIONS

Valatas, et al., "The value of experimental models of colitis in predicting efficacy of biological therapies for inflammatory bowel diseases", Am. J. Physiol Gastrointest Liver Physiol 305: G763-G785, 2013.
Whitepaper, "mdbiopoducts", Collagen Antibody Induced Arthritis, 10 pages (Aug. 2011).
Wu, et al., "Gene Biotechnology", Information Superhighway and Computer Databases of Nucleic Acids and Proteins 1997, 25 pages.
Xu, et al., "The Paradox Role of Regulatory T Cells in Ischemic Stroke", The Scientific World Journal, vol. 2013, 8 pages.
Blom, et al., "C4b-binding protein (C4BP) inhibits development of experimental arthritis in mice", Annals of the Rheumatic Diseases, vol. 68, No. 1, pp. 136-142. (Jul. 29, 2008).
Happonen, et al., "Complement Inhibitor C4b-Binding Protein Interacts Directly with Small Glycoproteins of the Extracellular Matrix", The Journal of Immunology, vol. 182, No. 3, pp. 1518-1525. (Jan. 2009).
Hardig, et al., "Expression and characterization of a recombinant C4b-binding protein lacking the B-chain", Biochemical Journal, vol. 308, No. 3, pp. 785-800. (Jan. 1995).
Hofmeyer, et al., "Arranged Sevenfold: Structural Insights into the C-Terminal Oligomerization Domain of Human C4b-Binding Protein", Journal of Molecular Biology, Academic Press, United Kingdom, vol. 425, No. 8, pp. 1302-1317. (Dec. 2012).
Dibell, "C4BP(β-): a therapeutic anti-inflammatory and immunemodulatory agent in autoimmunity", Retrieved from Internet, 30 pages. (downloaded Oct. 7, 2019) https://www.medicamentos-innovadores.org/sites/default/files/medinnovadores/Español/Farma-Biotech/Madrid_27-11-2013/Farmaindustria%20(26-11-13)(ARAN)%20(FINAL).pdf.
Kulak, et al., "The human serum protein C4b-binding protein inhibits pancreatic IAPP-induced inflammasome activation", Diabetologia, Springer, Berlin, DE, vol. 60, No. 8, pp. 152-153. (May 2017).
Olivar, et al., "The alpha7beta0 Isoform of the Complement Regulator C4b-Binding Protein Induces a Semimature, Anti-Inflammatory State in Dedritic Cells", The Journal of Immunology, vol. 190, No. 6, pp. 2857-2872. (Feb. 2013).
Reagan-Shaw, et al., "Dose translation from animal to human studies revisited", The FASEB Journal, Jan. 1, 2007 Federation of American Societies for Experimental Biology, vol. 22, pp. 659-661. (Mar. 2007).
Agarwal, et al., "A Novel Interaction between Complement Inhibitor C4bbinding Protein and Plasminogen That Enhances Plasminogen Activation", The Journal of Biological Chemistry, vol. 290, No. 30, pp. 18333-18342 (Jul. 24, 2015).
Allam, et al., "The role of innate immunity in autoimmune tissue injury", Current Opinion in Rheumatology 2008, 20:538-544.
Allam, et al., "Viral RNA and DNA Trigger Common Antiviral Responses in Mesangial Cells", J. Am. Soc. Nephrol 20: 1986-1996, 2009.
Alperovich, et al., "New immunosuppresor strategies in the treatment of murine lupus nephritis", Lupus (2007) 16, 18-24.
Altschul, "Amino Acid Substitution Matrices from an Information Theoretic Perspective", J. Mol.Biol. (1991) 291, 555-565.
Balkwill, et al., "Inflammation and cancer: back to Virchow?", Lancet 2001, 357: 539-545.
Berden, et al., "Role of nucleosomes for induction and glomerular binding of autoantibodies in lupus nephritis", Current Opinion in Nephrology and Hypertension, vol. 8(3), May 1999, pp. 299-306.
Blom, et al., "A Cluster of Positively Charged Amino Acids in the C4BP a-Chain is Crucial for C4b Binding and Factor I Cofactor Function", The Journal of Biological Chemistry, vol. 274, No. 27, Issue of Jul. 2, pp. 19237-19245, 1999.
Blom, "C4b-binding protein (C4BP) inhibits development of experimental arthritis in mice", Annals of the Rheumatic Diseases, published online Feb. 14, 2008.
Blom, et al., "Complement evasion strategies of pathogens—Acquisition of inhibitors and beyond", Molecular Immunology 46 (2009) 2808-2817.
Blom, et al., "Functions of human complement inhibitor C4b-binding protein in relation to its structure", Arch Immunol Ther Exp. 2004, 52, 83-95.
Brennan, et al., "Safety and immunotoxicity assessment of immunomodulatory monoclonal antibodies", mAbs, 2:3, 233-255; May/Jun. 2010; ISSN: 1942-0862 (Print) 1942-0870 (Online) Journal homepage: https://www.tandfonline.com/loi/kmab20.
Chen, et al., "Cytokine networks and T cell subsets in inflammatory bowel diseases", Inflamm Bowel Dis. May 2016, 22(5), 1157-1167.
Dahlback, "Purification of human C4b-binding protein and formation of its complex with vitamin K-dependent protein S", Biochem. J. (1983) 209, 847-856.
Danchenko, et al., "Epidemiology of systemic lupus erythematosus: a comparison of worldwide disease burden", Lupus (2006) 15, 308-318.
Ermert, et al., "C4b-binding protein: The good, the bad and the deadly, Novel functions of an old friend", Immunology Letters 169 (2016) 82-92.
Fakhouri, et al., "Treatment with human complement factor H rapidly reverses renal complement deposition in factor H-deficient mice", Kidney Int. Aug. 2010; 78(3): 279-286.
Feldmann, et al., "Rheumatoid Arthritis", Cell, vol. 85, 307-310, May 3, 1996.
Garrido-Mesa, et al., "The association of minocycline and the probiotic *Escherichia coli* Nissle 1917 results in an additive beneficial effect in a DSS model of reactivated colitis in mice", Biochemical Pharmacology 82 (2011) 1891-1900.
Garrido-Mesa, et al., "The intestinal anti-inflammatory effect of minocycline in experimental colitis involves both its immunomodulatory and antimicrobial properties", Pharmacological Research 63 (2011) 308-319.
Henikoff, et al., "Amino acid substitution matrices from protein blocks", Proc. Natl. Acad. Sci. USA, vol. 89, pp. 10915-10909, Nov. 1992.
Holdsworth, "Biologics for the treatment of autoimmune renal diseases", Nature Reviews/Nephrology, vol. 12, Apr. 2016, pp. 217-231.
Huang, et al., "Inflammation in stroke and focal cerebral ischemia", Surgical Neurology 66 (2006) 232-245.
Hui, et al., "Lupus nephritis: a 15-year multi-centre experience in the UK", Lupus (2013) 22, 328-332.
Jin, et al., "Inflammatory mechanisms in ischemic stroke: role of inflammatory cells", Journal of Leukocyte Biology, vol. 87, May 2010, pp. 779-789.
Jin, et al., "Inhibition of Breast Cancer Resistance Protein (ABCG2) in Human Myeloid Dendritic Cells Induces Potent Tolerogenic Functions during LPS Stimulation", PLOS One Aug. 2014 vol. 9, Issue 8, 11 pages.
Jin, et al., "Role of Inflammation and its Mediators in Acute Ischemic Stroke", J. of Cardiovasc. Trans, Res. (2013) 6:834-851.
Jovanovic, et al., "Fcc receptor biology and systemic lupus erythematosus", International Journal of Rheumatic Diseases 2009, 12:293-298.
Kannan, et al., "Animal models of rheumatoid arthritis and their relevance to human disease", Pathophysiology 12 (2005) 167-181.
Kariuki, et al., "Genetic Analysis of the Pathogenic Molecular Sub-phenotype Interferon Alpha Identifies Multiple Novel Loci Involved in Systemic Lupus Erythematosus", Genes Immun. 2015; 16(1) 15-23 (2015).
Kask, et al., "Structural Requirements for the Intracellular Subunit Polymerization of the Complement Inhibitor C4B-Binding Protein", Biochemistry 2002, 41, 9349-9357.
Kim, et al., "Investigating Intestinal Inflammation in DSS-induced Model of IBD", Journal of Visualized Experiments, Feb. 2012, 60, e3678, 6 pages.
Kono, et al., "Genetics of SLE in mice", Springer Semin. Immun. (2006) 28:83-96.
Korbet, et al., "Severe Lupus Nephritis: Racial Differences in Presentation and Outcome", J. Am. Soc. Nephrol. 18:244-254, 2007.

(56) References Cited

OTHER PUBLICATIONS

Luo, et al., "A Functional Variant in MicroRNA-146a Promoter Modulates Its Expression and Confers Disease Risk for Systemic Lupus Erythematosus", PLoS Genetics, Jun. 2011, vol. 7, Issue 6, pp. 1-11.
McInnes, et al., "The Pathogenesis of Rheumatoid Arthritis", N. Engl. J. Med., 2011: 365: 2205-19.
Melgar, et al., "Acute colitis induced by dextran sulfate sodium progresses to chronicity in C57BL/6 but not in BALB/c mice: correlation between symptoms and inflammation", Am. J. Physiol. Gastrointest. Liver Physiol. 288: G1328-1338, 2005.
Morelli, et al., "Dendritic cells: regulators of alloimmunity and opportunities for tolerance induction", Immunological Reviews 2003, vol. 196: 125-146.
Mortensen, et al., "Nephritogenic Potential of Anti-DNA Antibodies against Necro Nucleosomes", J. Am. Soc. Nephrol. 20, 696-704, 2009.
Nandakumar, et al., "Antibody-induced arthritis: disease mechanisms and genes involved at the effector phase of arthritis", Arthritis Research & Therapy 2006, 8:223, 11 pages.
Nicholas, et al., "Analysis and Visualization of Genetic Variation", embnet.news, vol. 4 Nr2, Jul. 31, 1997.
Olivar, et al., "The Complement Inhibitor Factor H Generates an Anti-Infammatory and Tolerogenic State in Monocyte-Derived Dendritic Cells", J. Immunol. 2016; 196:4274-4290, Apr. 2016.
Park, et al., "Inflammatory Bowel Diseases (IBD) immunopathogenesis: A comprehensive review of inflammatory molecules", Autoimmunity Reviews 16 (2017) 416-426.
Pei, "Inflammation in the pathogenesis of ischemic stroke", Frontiers in Bioscience, Landmark, 20, 772-783, Jan. 1, 2015.
Perry, et al., "MurineModels of Systemic Lupus Erythematosus Daniel", Journal of Biomedicine and Biotechnology, vol. 2011 pp. 1-19.
Perse, et al., "Dextran Sodium Sulphate ColitisMouseModel: Traps and Tricks", Journal of Biomedicine and Biotechnology, vol. 2012, Mar. 2012, 13 pages.
Porter, et al., "Human Immune Response to Recombinant Human Proteins", Journal of Pharmaceutical Sciences, vol. 90, No. 1, Jan. 2001, pp. 1-10.
Potempa, et al., "Binding of complement inhibitor C4b-binding protein contributes to serum resistance of Porphyromonas gingivalis1", J. Immunol., Oct. 15, 2008; 181(8): 6537-5544.
Rakoff-Nahoun, et al., "Why Cancer and Inflammation?", Yale Journal of Biology and Medicine 79 (2006), pp. 123-130.
Randhawa, et al., "A Review on Chemical-Induced Inflammatory Bowel Disease Models in Rodents", Korean J. Physiol. Pharmacol., vol. 18: 279-288, Aug. 2014.
Rodriguez, et al., "Reversal of Ongoing Proteinuria in Autoimmune Mice by Treatment With C-Reactive Protein", Arthritis & Rheumatism, vol. 52, No. 2, Feb. 2005, pp. 642-650.
Ross, "Modulation of drug resistance transporters as a strategy for treatingmyelodysplastic syndrome", Best Practice & Research Clinical Haemetology, vol. 17, No. 4, pp. 641-651, 2004.
Rottman, et al., "Mouse Models of Systemic Lupus Erythematosus Reveal a Complex Pathogenesis J.", Veterinary Pathology, 47(4), 664-676.
Shaukat Khan et al., "Dendritic Cells as Targets for Therapy in Rheumatoid Arthritis," Nat. Rev. Rheumatol. vol. 5, Oct. 2009, pp. 566-571, doi:10.1038/nrrheum.2009.185.
Frederic Coutant & Pierre Miossec, "Altered Dendritic Cell Functions in Autoimmune Diseases: Distinct and Overlapping Profiles," Nature Reviews | Rheumatology, vol. 12, Dec. 2016, pp. 703-715.
Immaculada Serrano et al., "The Hidden Side of Complement Regulator C4BP: Dissection and Evaluation of its Immunomodulatory Activity," Frontiers in Immunology, vol. 13, Apr. 2022, pp. 1-16, doi: 10.3389/fimmu.2022/883743.
Australian Examination Report for Application No. AU 2018247928, issued Feb. 8, 2023.
"Guidance for Industry: Estimating the Maximum Safe Starting Dose in Initial Clinical Trials for Therapeutics in Adult Healthy Volunteers," U.S. Department of Health and Human Services, Food and Drug Administration, Center for Drug Evaluation and Research (CDER), Jul. 2005.

* cited by examiner

A)

B)

C)

A)

B)

A)

B)

C4BP-BASED COMPOUNDS FOR TREATING IMMUNOLOGICAL DISEASES

FIELD OF THE INVENTION

The invention relates to the field of immunology and, more in particular, to the use of C4BP isoforms lacking beta chain and polypeptides comprising the CCP6 domain of the C4BP alpha chain for subcutaneous administration no more than once a week and at low doses to treat or prevent immunological diseases caused by an undesired activation of the immune system.

BACKGROUND OF THE INVENTION

The aberrant regulation of immune reactions has been associated with a wide array of human diseases, since the inappropriate mounting of an immune response against various self and foreign antigens plays a causal role in a huge number of pathologies including autoimmune disorders, asthma, allergic reactions, graft-versus-host disease, transplantation graft rejection and a variety of other immunological disorders. Rheumatoid arthritis, systemic lupus erythematosus or inflammatory bowel disease are examples of this group of disorders.

Rheumatoid arthritis (RA) is a systemic immune-mediated disorder characterized by chronic inflammation of the joints that is associated with persistent multiarticular synovitis, cartilage destruction, and even loss of joint function. Although remarkable progress has been made in the clinical treatment of RA, long-term administration of anti-rheumatic drugs still suffers quite a few drawbacks, including high dose and high frequency of drug use, as well as dysfunction of the heart, liver, kidney, and so forth.

The autoimmune disease systemic lupus erythematosus (SLE) affects approximately 70 per 100000 but varies between countries, populations and genders, with a 6-10 times increased frequency in women. SLE includes a range of manifestations from skin rashes, chronic fatigue and arthritis to the more severe glomerulonephritis, serositis and neurological involvement. Lupus nephritis is histologically evident in most patients with SLE. The symptoms of lupus nephritis are generally related to proteinuria, hypertension and renal failure. Most patients with SLE develop lupus nephritis early in their disease course. The present treatment involves the use of immunosuppressive agents such as cyclophosphamide, mycophenolate mofetil and calcineurin inhibitors. However, conventional immunosuppressors are not ideal in terms of efficacy and toxicity. Even the new biological and immunomodulatory agents tested to date directed against B cells (rituximab, ocrelizumab, belimumab, atacicept), co-stimulatory molecules (abatacept), T cells (alemtuzumab), cytokines (sirukumab, tocilizumab, etanercept) and components of the complement system (eculizumab), although more specific than corticoids and conventional immunosuppressors, still lack the efficacy and/or safety required for the clinical practice.

Human monocyte-derived dendritic cells (DCs) are activated by a pro-inflammatory stimulus and there is increasing evidence supporting the notion that dendritic cells may play a key role in the pathogenesis of a huge number of conditions related to autoimmunity and transplantation.

Dendritic cells (DC) are the professional APC of the immune system. At their immature stage, DC take up extracellular antigens by means of phagocytosis or pinocytosis and process the antigens to peptides in the endocytotic compartment such as endosomes and phagosomes, where peptides are bound to MHC class II molecules. They also have the unique ability of loading the peptides from exogenous proteins to the MHC class I pathway of presentation, a process called "cross-presentation". Given the appropriate differentiation signals (such as microbial products), immature DC may develop into an immunogenic DC which is equipped with the ability to activate both naive and memory T cells. On the other side of the spectrum immature DC can also differentiate into a tolerogenic phenotype, which is thought to play a crucial role in the maintenance of peripheral tolerance (Steinman, Ann. Rev. Immunol. 2003, 21: 685-711; Morelli, Immunol Rev 2003: 125-146).

WO2013/010998 A2 discloses that C4b-binding protein (C4BP) isoforms lacking beta chain down-regulate the activation phenotype of human monocyte derived dendritic cells (Mo-DCs) inducing a tolerogenic state in dendritic cells; and that the CCP6 domain of C4BP is necessary for the tolerogenic activity of C4BP over human Mo-DCs.

Blom et al. (Blom A. M., et al. Ann Rheum Dis 2009; 68:136-142) discloses that C4BP inhibits development of experimental arthritis in mice by inhibition of the complement. However, human C4BP is cleared fast from the circulation and the authors of this study had to administer high doses of C4BP (2 mg/mouse) intraperitoneally once every two days to achieve therapeutic effect.

Therefore, there is a need for alternative methods of treatment of immunological diseases that overcome the drawbacks of existing therapies, particularly the use of a high dose and high frequency of administration.

SUMMARY OF THE INVENTION

In a first aspect, the invention relates to a compound selected from the group consisting of:

a) a C4BP isoform lacking the beta chain wherein if at least one of the alpha-chains forming said isoform is a deletion mutant which lacks at least one of the CCP domains, the CCP6 domain is preserved in said alpha-chain;

b) a polypeptide comprising a full-length C4BP alpha-chain or a deletion mutant thereof that preserves the CCP6 domain; and c) a polypeptide comprising the CCP6 domain of the C4BP alpha-chain or a functionally equivalent variant of said CCP6 domain for use in the prevention and/or treatment of an immunological disease caused by an undesired activation of the immune system, wherein the compound is administered subcutaneously in a regimen comprising a plurality of administrations and wherein the compound is administered no more than once a week.

In a second aspect, the invention relates to a compound selected from the group consisting of:

a) a C4BP isoform lacking the beta chain wherein if at least one of the alpha-chains forming said isoform is a deletion mutant which lacks at least one of the CCP domains, the CCP6 domain is preserved in said alpha-chain;

b) a polypeptide comprising a full-length C4BP alpha-chain or a deletion mutant thereof that preserves the CCP6 domain; and c) a polypeptide comprising the CCP6 domain of the C4BP alpha-chain or a functionally equivalent variant of said CCP6 domain for use in the prevention and/or treatment of an immunological disease caused by an undesired activation of the immune system, wherein the compound is administered subcutaneously at a dose of from 0.24 mg/$m^2$ to 9.99 mg/$m^2$.

In another aspect, the invention relates to a pharmaceutical composition comprising from 0.45 mg to 18.90 mg of a compound selected from the group consisting of:

(a) a C4BP isoform lacking the beta chain wherein if at least one of the alpha-chains forming said isoform is a deletion mutant which lacks at least one of the CCP domains, the CCP6 domain is preserved in said alpha-chain;

(b) a polypeptide comprising a full-length C4BP alpha-chain or a deletion mutant thereof that preserves the CCP6 domain; and (c) a polypeptide comprising the CCP6 domain of the C4BP alpha-chain or a functionally equivalent variant of said CCP6 domain and a pharmaceutically acceptable excipient suitable for subcutaneous administration for use in the prevention and/or treatment of an immunological disease caused by an undesired activation of the immune system, wherein the pharmaceutical composition is administered subcutaneously.

DETAILED DESCRIPTION OF THE INVENTION

Figure 5:
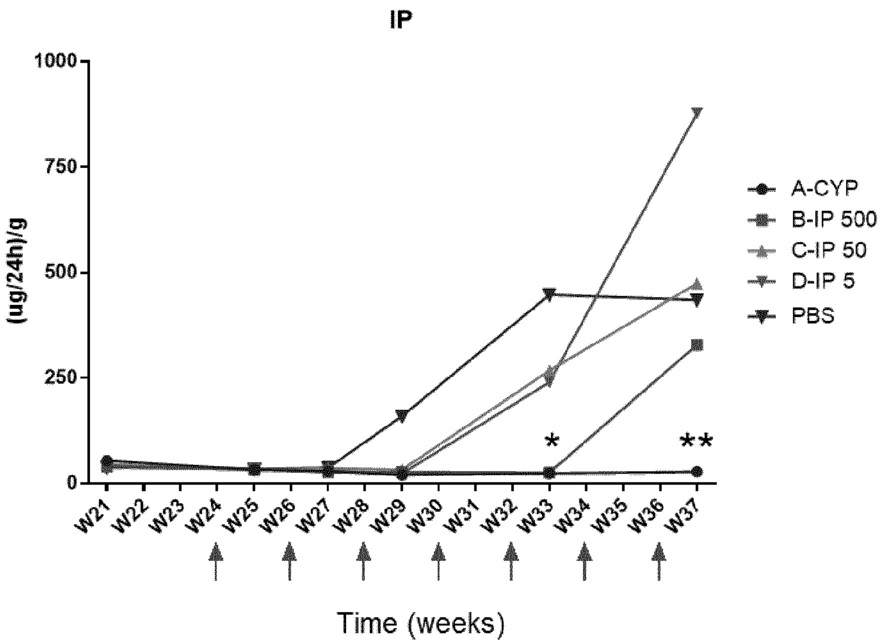
FIG. 5. Renal function determination in lupus-prone NZBWF1 mice. Total 24-h urinary protein was determined by Pyrogallol Red-molybdate protein dye-binding assay. rC4BP(β−) administration was performed intraperitoneally (IP) (A), or subcutaneously (SC) (B), according to the indicated dose (5 μg/mouse, 50 μg/mouse or 500 μg/mouse). Arrows identify the rC4BP(β−) inoculation schedule, once every two weeks, starting from week 24, except for the "H-SC 500e" group, which underwent monthly administration. CYP administration was performed at 50 mg/kg, once every 10 days. Data are normalized by mouse weight and expressed as mean±SD (n=6-8); *$p<0.05$; **$p<0.01$, compared with control PBS-inoculated mice.
Figure 5:
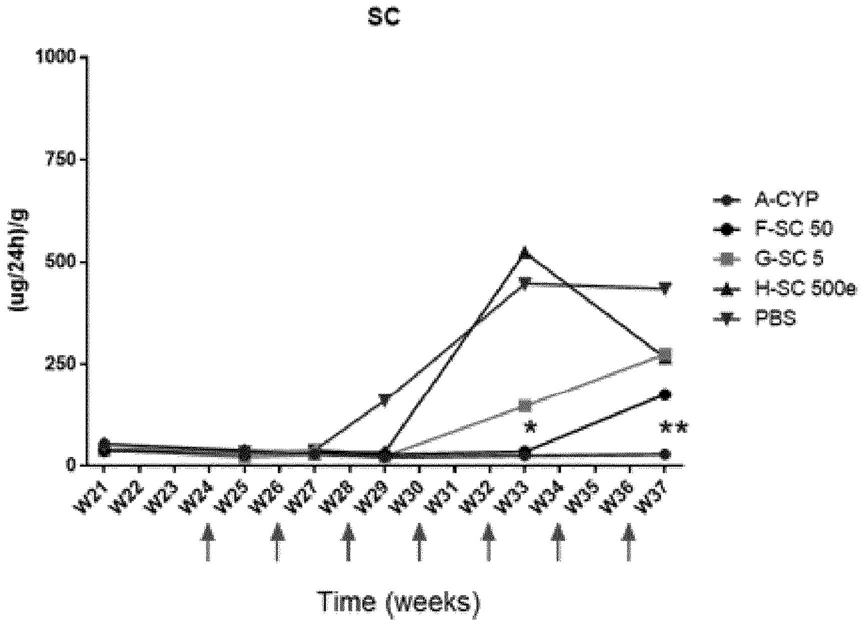
Figure 6:
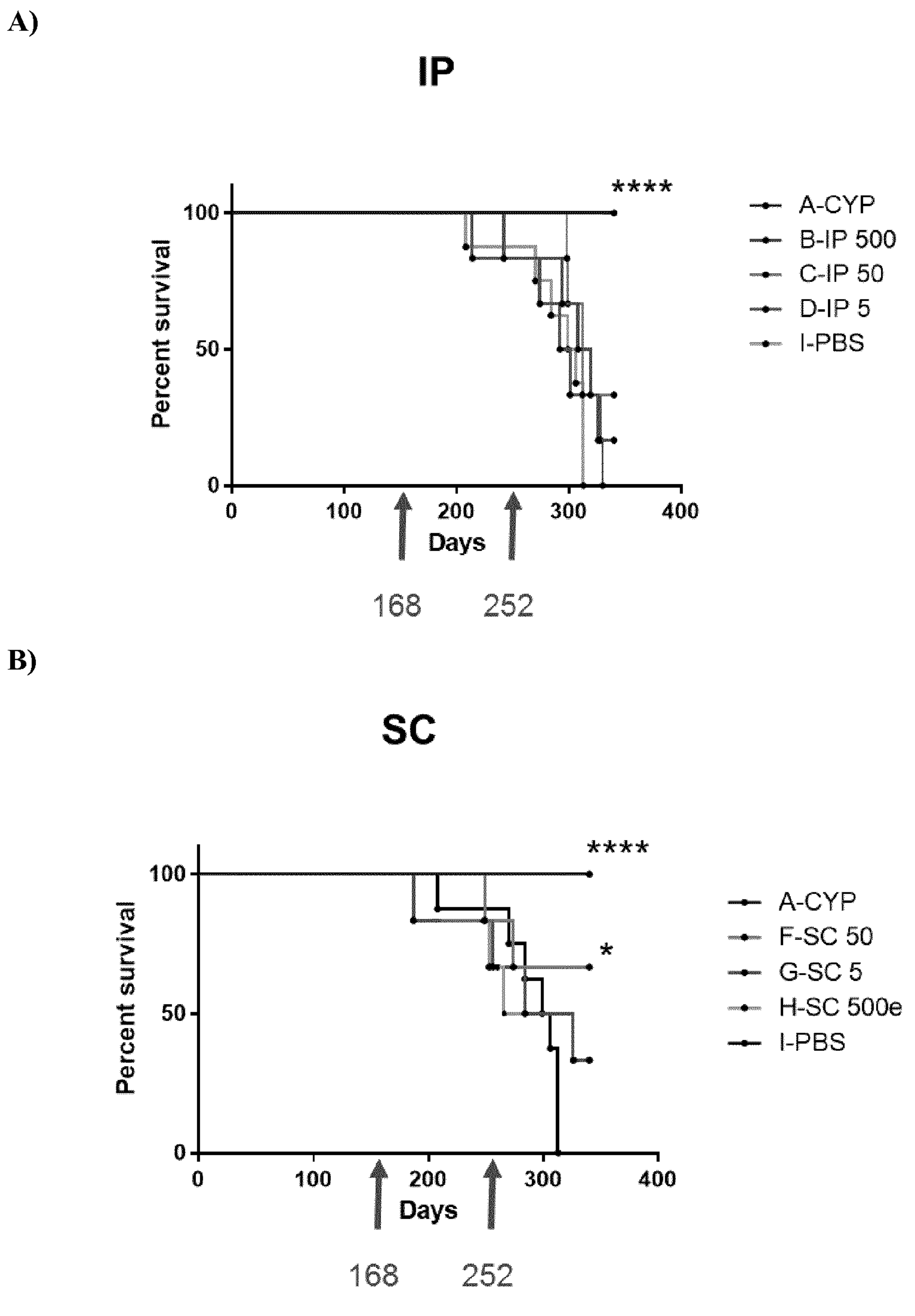
FIG. 6. Kaplan-Meier survival curves from lupus-prone NZBWF1 mice. Cumulative survival curves showed increased survival in the CYP-treated and in some of the rC4BP(β−)-treated groups. rC4BP(β−) was administered once every two weeks intraperitoneally (IP) (A), or subcutaneously (SC) (B), according to the indicated dose (5 μg/mouse, 50 μg/mouse or 500 μg/mouse) except for the "H-SC 500e" group, which underwent monthly administration. Arrows identify the starting (day 168) and the end (day 252) of the treatment period. CYP administration was performed at 50 mg/kg, once every 10 days. n=6/group; *$p=0.05$; ****$p<0.0001$, compared with control PBS-inoculated mice (I-PBS); long-rank test.

The authors of the present invention have surprisingly found that subcutaneous administration of recombinant C4BP isoform lacking the β-chain (rC4BP(β−)) at low doses such as 50 μg once every two weeks lead to the strongest attenuation of proteinuria development, as end-point for renal function, and best survival rate in a mouse model of systemic lupus erythematosus (SLE) (see Example 2 and FIGS. 5-6). Even more surprising, the inventors have demonstrated that the subcutaneous administration of 50 μg/mouse is more effective than the intraperitoneal administration of 500 μg/mouse with the same regimen. The inventors have also shown the efficacy of C4BP(β−) administered at low doses and low frequency for other immunological diseases such as rheumatoid arthritis (see Example 3) wherein (rC4BP(β−)) is effective for at least one week.

These results shown that, despite the fact that C4BP is known to have a transient effect because two days after its intraperitoneal administration only 3% of the initial amount remains in the circulation (Blom A. M., et al. Ann Rheum Dis 2009; 68:136-142), it is possible to design a therapeutic regimen for the treatment of immunological diseases by administering subcutaneously C4BP(β−) at reduced doses and/or less frequency of administration than expected knowing its pharmacokinetic.

Therapeutic Uses of C4BP Isoforms Lacking the Beta Chain and Polypeptides Comprising the CCP6 Domain of the Alpha Chain of C4BP at Low Frequency of Administration The authors have demonstrated that the subcutaneous administration of a C4BP isoform lacking beta chain is effective in the treatment of several immunological diseases including systemic lupus erythematosus, lupus nephritis and rheumatoid arthritis and that the effect is maintained for at least one week.

Thus, in a first aspect, the invention relates to a compound selected from the group consisting of:

a) a C4BP isoform lacking the beta chain wherein if at least one of the alpha-chains forming said isoform is a deletion mutant which lacks at least one of the CCP domains, the CCP6 domain is preserved in said alpha-chain;

b) a polypeptide comprising a full-length C4BP alpha-chain or a deletion mutant thereof that preserves the CCP6 domain; and c) a polypeptide comprising the CCP6 domain of the C4BP alpha-chain or a functionally equivalent variant of said CCP6 domain for use in the prevention and/or treatment of an immunological disease caused by an undesired activation of the immune system, wherein the compound is administered subcutaneously in a regimen comprising a plurality of administrations and wherein the compound is administered no more than once a week.

In another aspect, the invention relates to the use of a compound selected from the group consisting of:

a) a C4BP isoform lacking the beta chain wherein if at least one of the alpha-chains forming said isoform is a deletion mutant which lacks at least one of the CCP domains, the CCP6 domain is preserved in said alpha-chain;

b) a polypeptide comprising a full-length C4BP alpha-chain or a deletion mutant thereof that preserves the CCP6 domain; and c) a polypeptide comprising the CCP6 domain of the C4BP alpha-chain or a functionally equivalent variant of said CCP6 domain for the manufacture of a medicament for the prevention and/or treatment of an immunological disease caused by an undesired activation of the immune system, wherein the compound is administered subcutaneously in a regimen comprising a plurality of administrations and wherein the compound is administered no more than once a week.

In another aspect, the invention relates to a method for the prevention and/or treatment of an immunological disease caused by an undesired activation of the immune system in a subject in need thereof comprising the administration to said subject of a compound selected from the group consisting of:

a) a C4BP isoform lacking the beta chain wherein if at least one of the alpha-chains forming said isoform is a deletion mutant which lacks at least one of the CCP domains, the CCP6 domain is preserved in said alpha-chain;

b) a polypeptide comprising a full-length C4BP alpha-chain or a deletion mutant thereof that preserves the CCP6 domain; and c) a polypeptide comprising the CCP6 domain of the C4BP alpha-chain or a functionally equivalent variant of said CCP6 domain and wherein said compound is administered subcutaneously in a regimen comprising a plurality of administrations and wherein the compound is administered no more than once a week.

It is known that C4BP isoforms lacking the beta chain (C4BP(β−)) down-regulate the activation phenotype of human Mo-DCs and promote the generation of dendritic cells which show features of tolerogenic dendritic cells, thus being useful in the treatment of immunological diseases caused by an undesired activation of the immune system in which dendritic cells are involved (WO 2013/010998 A2). Furthermore, it has been demonstrated that the CCP6 domain of the C4BP alpha-chain is necessary for the tolerogenic activity of (C4BP(β−)) and that peptides consisting of mutants of the CCP6 domain retain said tolerogenic activity (Olivar et al. 2013. J. Immunol., 190:2857-2872).

Figure 3:
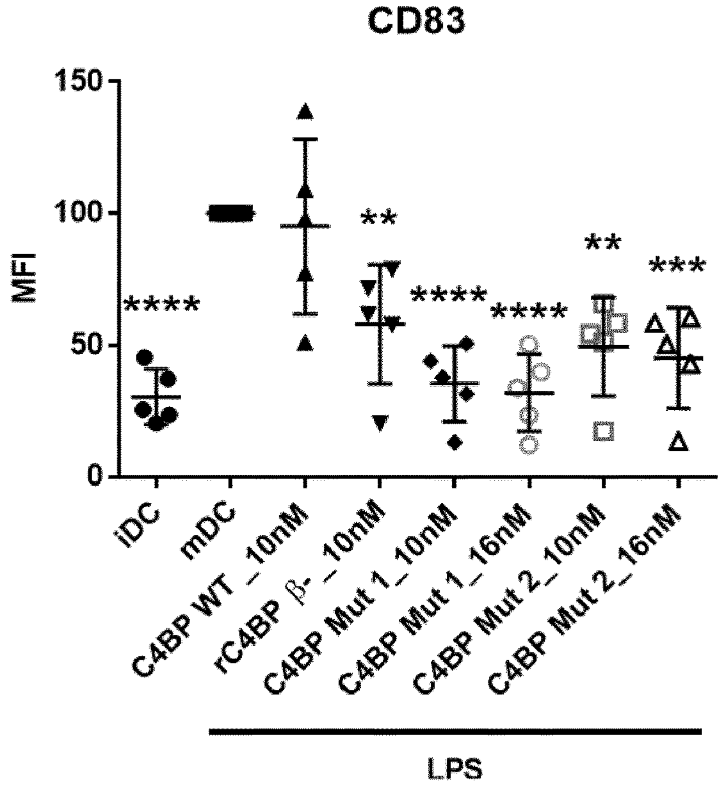
FIG. 3. Functional evaluation of the immunomodulatory activity of rC4BP(β−) and its engineered variants on human monocyte-derived DCs. Human DCs were incubated throughout their differentiation and maturation process with wild type recombinant C4BP(β−) (rC4BP(β−), or its deletion mutants 1 and 2 at the indicated concentrations (in nM). DC maturation was achieved by LPS treatment. Cells were then collected, washed and analyzed by flow cytometry for cell-surface expression of the maturation marker CD83 (A), and the co-stimulatory molecule CD86 (B). The relative median fluorescence intensities (MFI) for CD83 and CD86 cell-surface expression are indicated. Moreover, the respective cell supernatants were also collected and the release of the pro-inflammatory cytokine IL-12 (hIL-12p70) was assessed by ELISA (C). Results shown are the mean±SD from five independent blood donors. iDC, untreated immature DCs; mDC, untreated, LPS-matured DCs; C4BP WT (plasma-purified C4BP(β+) isoform-treated and LPS-matured DCs); rC4BP(β−) (recombinant C4BP(β−)) isoform-treated and LPS-matured DCs; C4BP Mut, C4BP(β−) deletion mutant-treated and LPS-matured DCs. *$p<0.05$, $p<0.01$, *$p<0.001$, ****$p<0.0001$ compared with mDC.
Figure 3:
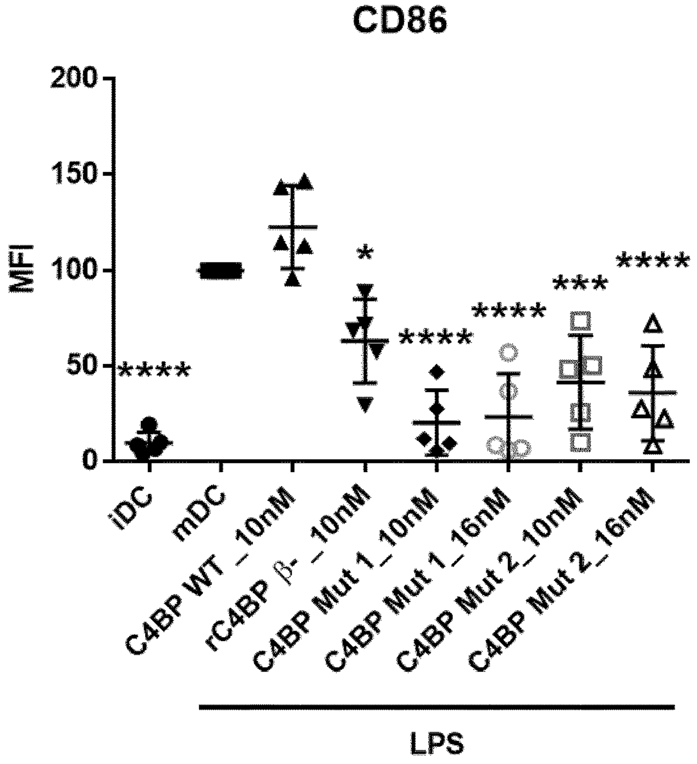
Figure 3:
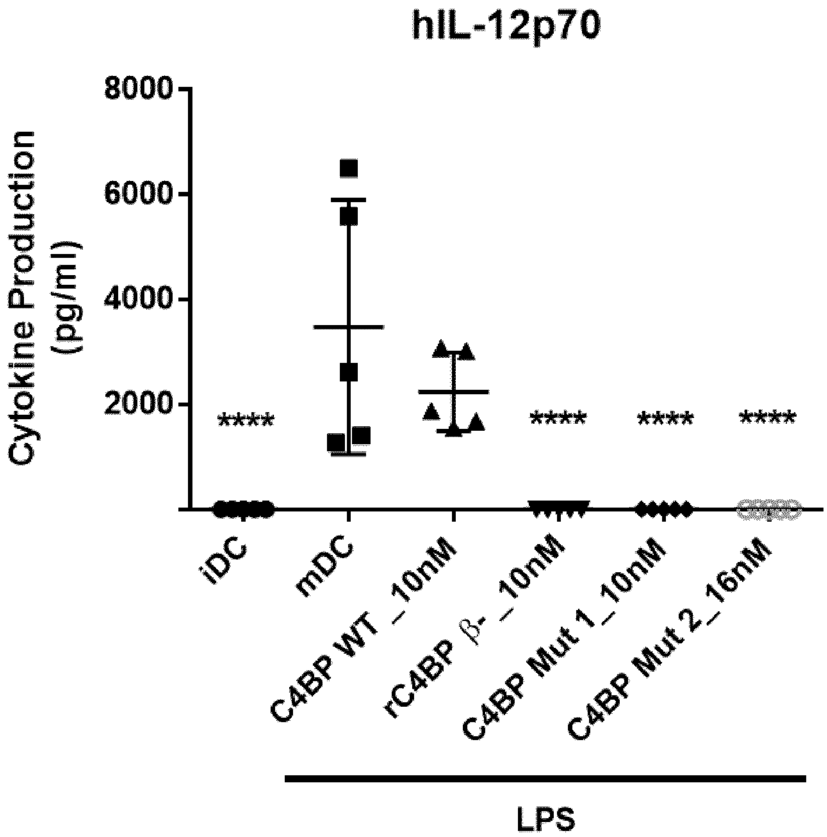

The inventors have demonstrated that a C4BP isoform having full-length alpha-chains and lacking the beta chain has immunomodulatory activity (Example 1). The inventors have also shown that oligomers formed by deletion mutants of alpha-chains that preserve the CCP6 domain retain the immunomodulatory activity (Example 1 and FIG. 3).

Therefore, the compound of the invention can be an oligomer of full-length C4BP alpha-chains lacking the beta chain or an oligomer of deletion mutants of C4BP alpha-chain lacking the beta chain in which the CCP6 domain is preserved.

Therefore, in an embodiment according to item (a) of the first aspect of the invention, the compound of the invention is a C4BP isoform lacking the beta chain wherein if at least one of the alpha-chains forming said isoform is a deletion mutant which lacks at least one of the CCP domains, the CCP6 domain is preserved in said alpha-chain.

The term "C4BP", as used herein, refers to "C4b-binding protein" which is a regulatory component of the classical pathway that is mainly synthesized by liver cells which acts as a cofactor for Factor I-dependent degradation of C3b and C4b and accelerates the decay of classical pathway C3/C5-convertases. C4BP is a large 500 kDa multimeric protein that has several identical 75 kDa α-chains and often also one 40 kDa β-chain. C4BP circulates in the plasma as three isoforms, the proportion of which depends on the relative levels of C4BPα (70 kDa) and C4BPβ (45 kDa) chains. The major isoform of C4BP is composed of 7 identical α-chains and 1 β-chain ($\alpha_7\beta_1$), whereas upon inflammation a normally less abundant isoform is up-regulated that is exclusively composed of α-chains ($\alpha_7\beta_0$). Moreover, recombinant expression of the α-chains in eukaryotic cells results in oligomer comprising 6 α-chains ($\alpha_6\beta_0$). Thus, the term "C4BP isoform" in the context of the present invention refers to any oligomer resulting from the association of a plurality of C4BP α-chains and which is devoid of β-chain.

The skilled person will understand that C4BP isoforms lacking a β chain may be formed exclusively by α-chains as they naturally occur in nature (e.g. human, mouse, rat, or bovine C4BP α-chain) as defined below or may contain one or more α-chain variants. For instance, the C4BP isoforms lacking 3 chain may contain at least one, at least two, at least three, at least four, at least five, at least six α-chain variants (in the case that the C4BP isoform is the $\alpha_6\beta_0$) or at least one, at least two, at least three, at least four, at least five, at least six or at least seven α-chain variants (in the case that the C4BP isoform is the $\alpha_7\beta_0$). If the isoform contains more than one α-chain variants, said variants can be different to each other or identical.

The term "C4BP α-chain", also known as PRP or proline-rich protein, as used herein, refers to the mature processed form of the human polypeptide defined under accession number P04003 in the NCBI database (release of Apr. 5, 2011) and which comprises amino acids 49 to 597. The term C4BP α-chain is also used to refer to orthologs of the human C4BP α-chain such as the mouse C4BP α-chain corresponding to the mature form of the polypeptide shown in the NCBI database under accession number P08607 (amino acids 57 to 469), the rat C4BP α-chain corresponding to the mature form of the polypeptide shown in the NCBI database under accession number Q63514 (amino acids 14 to 558), or the bovine C4BP α-chain corresponding to the mature form of the polypeptide shown in the NCBI database under accession number Q28065 (amino acids 49 to 610).

The C4BP α-chain contains 8 complement control protein domains (CCP). The C-terminal extensions of both α- and β-chains contain 2 cysteine residues each and an amphipatic α helix region, which is required for intracellular polymerization of the molecule.

The term "CCP domain", as used herein, refers to one of the complement control domain found in the C4BP alpha chain. The CCP are 60 amino acid residues long comprising four cysteine residues disulfide bonded in a 1-3 2-4 arrangement and a hydrophobic core built around an almost invariant tryptophan residue.

The CCP6 domain corresponds to the region found between amino acids 363 and 424 with respect to the human C4BP alpha chain defined in the sequence provided in the NCBI database under accession number P04003 (SEQ ID NO:1) and which corresponds to the sequence:

```
                                        (SEQ ID NO: 1)
LCCPEPKLNN GEITQHRKCR PANHCVYFYG DEISFSCHET

CRFSAICQGD GTWSPRTPSC GD
```

In an embodiment, the C4BP isoform lacking the beta chain is an isoform formed by alpha-chains wherein at least one of the alpha-chains, preferably all, comprises the CCP6 domain but does not comprise any of the other CCP domains of the C4BP alpha-chain. In another embodiment, the C4BP isoform lacking the beta chain is an isoform formed by alpha-chains wherein at least one of the alpha-chains, preferably all, consists of the CCP6 domain of C4BP.

The C4BP isoforms lacking the beta chain of the invention may contain variants of the naturally-occurring C4BP α-chains. Therefore, the term "C4BP α-chain" is also used in the context of the isoform of the invention, to refer to any variant of the naturally-occurring C4BP α-chains defined above resulting from the modification, insertion or deletion of one or more amino acids and which substantially preserves the ability to form oligomers with other C4BP α-chain or variants thereof. Methods for determining whether a variant is capable of forming oligomers are available to the skilled person and include, for instance, a method as described by Blom et al. (J. Biol. Chem. 2001, 276: 27136-27144) based on the analysis by polyacryamide gel electrophoresis under native conditions of a purified C4BP obtained by recombinant expression of the variant α-chain in eukaryotic cell (e.g. 293 cells) followed by affinity purification using an antibody specific for one of the CCP regions which has not been deleted.

In a preferred embodiment, the C4BP isoform lacking the beta chain is selected from the group consisting of $\alpha_7\beta_0$, $\alpha_6\beta_0$ and combinations thereof.

C4BP α-chain variants for use according to the present invention include, without limitation:

Naturally-occurring polymorphic variants (i.e., allelic variants) as well as recombinantly manipulated or engineered α-chain variants. Variant C4BP α-chains suitable for use according to the present invention include, without limitation, polypeptides having at least 99%, at least 98%, at least 97%, at least 96%, at least 95%, at least 94%, at least 93%, at least 92%, at least 91%, at least 90%, at least 85%, at least 80%, at least 75%, at least 70%, at least 65%, at least 60%, at least 55%, at least 50% identity with the naturally-occurring C4BP α-chain polypeptides as defined above and, in particular, with the naturally-occurring C4BP α-chain of human origin.

The percent identity of the amino acid sequence of a C4BP α-chain variant to the amino acid sequence set forth above can be readily determined by persons skilled in the art by sequence comparison. As used herein, two amino acid sequences have 100 percent amino acid sequence identity if the amino acid residues of the two amino acid sequences are the same when aligned for maximal correspondence. Sequence comparisons of polypeptides and polynucleotides (for example, the polynucleotides that encode the polypeptides described herein) can be performed using any method such as those that use computer algorithms well known to persons having ordinary skill in the art. Such algorithms include Align or the BLAST algorithm (see, e.g., Altschul, J. Mol. Biol. 219:555-565, 1991; Henikoff and Henikoff, Proc. Natl. Acad. Sci. USA 89:10915-10919, 1992), which are available at the NCBI website (see [online] Internet at ncbi.nlm.nih-.gov/cgi-bin/BLAST). Default parameters may be used. In addition, standard software programs are available, such as those included in the LASERGENE bioinformatics computing suite (DNASTAR, Inc., Madison, Wis.); CLUSTALW program (Thompson et al., Nucleic Acids Res. 22:4673-80 (1991)); and "GeneDoc" (Nicholas et al., EMBNEW News 4:14 (1991)). Other methods for comparing two amino acid sequences by determining optimal alignment are practiced by persons having skill in the art (see, for example, Peruski and Peruski, The Internet and the New Biology: Tools for Genomic and Molecular Research (ASM Press, Inc. 1997); Wu et al. (eds.), "Information Superhighway and Computer Databases of Nucleic Acids and Proteins," in Methods in Gene Biotechnology, pages 123-151 (CRC Press, Inc. 1997); and Bishop (ed.), Guide to Human Genome Computing, 2nd Ed. (Academic Press, Inc. 1998)).

Deletion mutants which lack at least one of the CCP regions provided that the CCP6 domain is preserved (see example 1) such as, for instance, mutants lacking the CCP1 domain, lacking the CCP2 domain, lacking the CCP3 domain, lacking the CCP4 domain, lacking the CCP5 domain, lacking the CCP7 domain and/or lacking the CCP8 domain.

Fusion proteins comprising a first region which comprises the C4BP α-chain and a second region which comprises a polypeptide which does not form part of the C4BP alpha chain. The fusion protein of the present invention may comprise in an amino terminal to carboxy terminal direction, (a) the region which comprises the CCP6 domain and (b) the region which comprises a polypeptide which does not form part of the C4BP alpha chain. Alternatively, the fusion protein of the invention may comprise in an amino terminal to carboxy terminal direction, (a) the region which comprises a polypeptide which does not form part of the C4BP alpha chain and (b) the region which comprises the CCP6 domain. Examples of fusion proteins that improve pharmacokinetic properties include, without limitation, fusions to human albumin, an immunoglobulin Fc region, Fc domains, poly Glu or poly Asp sequences, ferritin and transferrin. Additionally, fusion with conformationally disordered polypeptide sequences composed of the amino acids Pro, Ala, and Ser ('PASylation') or hydroxyethyl starch (HESylation®) provides a simple way to increase the hydrodynamic volume of the C-peptide. This additional extension adopts a bulky random structure, which significantly increases the size of the resulting fusion protein. In a preferred embodiment, the region which comprises a polypeptide which does not form part of the C4BP alpha chain is an immunoglobulin Fc region.

As used herein, the term, "immunoglobulin Fc region" is understood to mean the carboxyl-terminal portion of an immunoglobulin chain constant region, preferably an immunoglobulin heavy chain constant region, or a portion thereof. For example, an immunoglobulin Fc region may comprise 1) a CH1 domain, a CH2 domain, and a CH3 domain, 2) a CH1 domain and a CH2 domain, 3) a CH1 domain and a CH3 domain, 4) a CH2 domain and a CH3 domain, or 5) a combination of two or more CH domains and an immunoglobulin hinge region. The immunoglobulin Fc region of the fusion protein of the present invention preferably comprises or consists of an Fc or a portion of an Fc of an immunoglobulin of isotype selected from IgG, IgM, IgA, IgD, IgE, further preferably, IgG1, IgG2, IgG3, IgG4, IgA1, IgA2, sIgA, more preferably IgG2 or IgG4, most preferably IgG2.

In a preferred embodiment, the variant is a deletion mutant.

The authors have demonstrated that deletion mutants lacking domains that retain the complement inhibitory activity or having mutated the domain responsible of plasminogen binding retain the immunomodulatory activity (Example 1).

Therefore, in a preferred embodiment, the deletion mutant is a mutant in which at least one of the CCP1, CCP2, CCP3, CCP4 and/or CCP8 domains is deleted; preferably is a mutant in which CCP1, CCP2 and CCP3 domains are deleted; more preferably is a mutant in which CCP1, CCP2, CCP3 and CCP4 domains are deleted. In another embodiment, the deletion mutant is a mutant in which the CCP8 domain is deleted; preferably a mutant in which CCP1, CCP2, CCP3 and CCP8 are deleted; more preferably a mutant in which CCP1, CCP2, CCP3, CCP4 and CCP8 are deleted. The deletion of these domains is a complete deletion, in which the complete domain is removed.

The invention also contemplates deletion mutants in which the deletion of a domain is not complete (i.e. only part of the domain is deleted, preferably the part involved in the complement inhibitory activity and/or responsible of plasminogen binding). Therefore, in a preferred embodiment, the deletion mutant is a mutant in which at least one of the CCP regions is partially deleted provided that the CCP6 region is preserved such as, for instance, mutants lacking partially the CCP1 domain, lacking partially de CCP2 domain, lacking partially the CCP3 domain, lacking partially the CCP4 domain, lacking partially the CCP5 domain, lacking partially the CCP7 domain and/or lacking partially the CCP8 domain. In another embodiment, at least one of the CCP1, CCP2, CCP3, CCP4 and/or CCP8 is partially deleted; preferably is a mutant in which CCP1, CCP2 and CCP3 domains are partially deleted; more preferably is a mutant in which CCP1, CCP2, CCP3 and CCP4 domains are partially deleted. In another embodiment, the deletion mutant is a mutant in which the CCP8 domain is partially deleted; preferably a mutant in which CCP1, CCP2, CCP3 and CCP8 are partially deleted; more preferably a mutant in which CCP1, CCP2, CCP3, CCP4 and CCP8 are partially deleted.

It is known that a cluster of positively charged amino acids in the C4BP alpha-chain CCP1 and CCP2 is crucial for C4b binding and factor I cofactor function, particularly the residues $Arg^{39}$, $Arg^{64}$ and $Arg^{66}$ (Blom A. M. et al. 1999. J Biol Chem, 274(27):19237-19245) and that CCP1-CCP3 of C4BP alpha-chain contribute to the binding of C4b (Blom A. M. et al. 2001. J Biol Chem, 276(29):27136-27144). It has also been disclosed that the CCP8 of C4BP alpha-chain mediates the interaction with plasminogen, primarily due to the lysine residues (Agarwal V. et al. 2015. J. Biol. Chem, 290(30): 18333-42).

The invention also contemplates variants in which domains that retain the complement inhibitory activity and/or domains responsible of plasminogen binding are mutated, preferably are mutated to abolish said activity. In a preferred embodiment, the variants of the C4BP alpha-chain are variants in which at least one of the CCP1, CCP2, CCP3, CCP4 and/or CCP8 domains is mutated; preferably is a variant in which CCP1, CCP2 and CCP3 domains are mutated; more preferably is a variant in which CCP1, CCP2, CCP3 and CCP4 domains are mutated. In another embodiment, the variant is a variant in which the CCP8 domain is mutated; preferably a variant in which CCP1, CCP2, CCP3 and CCP8 are mutated; more preferably a variant in which CCP1, CCP2, CCP3, CCP4 and CCP8 are mutated.

In a more preferred embodiment, the variant of the C4BP alpha-chain is a variant in which at least one of the Lys residues of the CCP8 domain is mutated. Preferably, at least one of the Lys residues of the CCP8 domain has been replaced by a residue selected from the group consisting of Pro, Asp, Glu, His, Ile, Ala, Ser, Thr, Val, Gin and Asn; preferably selected from Gin and Asn; more preferably Gln. In a more preferred embodiment, the three Lys residues of the CCP8 domain are each replaced by a residue selected from the group consisting of Pro, Asp, Glu, His, Ile, Ala, Ser, Thr, Val, Gin and Asn; preferably selected from Gin and Asn; more preferably Gin.

In another embodiment, the variant is a variant in which at least one of the CCP1, CCP2, CCP3 and/or CCP4 domains are completely or partially deleted and in which at least one of the Lys residue of CCP8 is replaced by a residue selected from the group consisting of Pro, Asp, Glu, His, Ile, Ala, Ser, Thr, Val, Gin and Asn; preferably selected from Gin and Asn; more preferably Gin. In a more preferred embodiment, the variant is a variant in which the CCP1, CCP2 and CCP3 domains are completely deleted and the three Lys residues of CCP8 are each replaced by a residue selected from the group consisting of Pro, Asp, Glu, His, Ile, Ala, Ser, Thr, Val, Gin and Asn; preferably selected from Gin and Asn; more preferably Gin. In a more preferred embodiment, the variant is a variant in which the CCP1, CCP2, CCP3 and CCP4 domains are completely deleted and the three Lys residues of CCP8 are each replaced by a residue selected from the group consisting of Pro, Asp, Glu, His, Ile, Ala, Ser, Thr, Val, Gin and Asn; preferably selected from Gin and Asn; more preferably Gin. In an even more preferred embodiment, the CCP1, CCP2, CCP3 and CCP4 domains are completely deleted and the three Lys residues of CCP8 are replaced by Gin.

The invention also contemplates the use of polypeptides that do not form oligomers.

Therefore, in a preferred embodiment according to item (b) of the first aspect of the invention, the compound to be used in the invention is a polypeptide comprising a full-length C4BP alpha-chain or a deletion mutant thereof that preserves the CCP6 domain.

The expression "polypeptide", as used in the context of the present invention, refers to polymeric forms of amino acids of any length, encompassing both polypeptides and peptides, and relates to a linear chain of more than 2 amino acids joined together by peptide bonds.

The expression "full-length C4BP alpha-chain" refers to an alpha-chain that contains all the CCP present in a naturally occurring C4BP (i.e. CCP1, CCP2, CCP3, CCP4, CCP5, CCP6, CCP7 and CCP8). The expression "full-length C4BP alpha-chain" also refers to full-length C4BP alpha-chain variants of the naturally-occurring C4BP alpha-chains defined above resulting from the modification, insertion or deletion of one or more amino acids. In an embodiment, said variants of the full-length C4BP alpha-chain are not capable of forming oligomers with other C4BP alpha-chain or variants thereof. Full-length C4BP alpha-chain variants can be naturally occurring polymorphic variants (i.e. allelic variants) as well as recombinantly manipulated or engineered alpha-chain variants. Variants of the full-length C4BP alpha-chain suitable for use according to the present invention include, without limitation, polypeptides having at least 99%, at least 98%, at least 97%, at least 96%, at least 95%, at least 94%, at least 93%, at least 92%, at least 91%, at least 90%, at least 85%, at least 80%, at least 75%, at least 70%, at least 65%, at least 60%, at least 55%, at least 50% identity with the naturally-occurring C4BP α-chain polypeptides as defined above and, in particular, with the naturally-occurring C4BP α-chain of human origin. The percent identity of the amino acid sequence may be calculated as disclosed above.

Compounds that also can be used according to item (b) of the present invention are polypeptides comprising deletion mutants of a full-length C4BP alpha-chain that preserve the CCP6 domain. The same deletion mutants disclosed for item (a) of the first aspect of the invention are also applicable to item (b) of the first aspect of the invention, with the exception that the polypeptides comprising said deletion mutants are not forming oligomers.

In an embodiment, the polypeptide comprising a deletion mutant of the full-length C4BP alpha-chain that preserves the CCP6 domain may be selected from the group consisting of:

- a polypeptide comprising the CCP5, CCP6 and CCP7 domains of the C4BP alpha chain but lacking the one or more of any of the other CCP domains found in the C4BP alpha chain and, in particular, lacking CCP8 and
- a polypeptide comprising the CCP5, CCP6 and CCP7 domains of the C4BP alpha chain and wherein said polypeptide does not comprise a region of a protein different from C4BP.

The polypeptides according to item (b) of the first aspect of the invention can comprise regions not forming part of C4BP alpha chain. Particularly, said polypeptides may be fusion proteins as disclosed above in the context of item (a) of the first aspect of the invention, with the exception that the compound administered is not an oligomer.

In another preferred embodiment, according to item (c) of the first aspect of the invention, the invention relates to a polypeptide comprising the CCP6 domain of the C4BP alpha-chain or a functionally equivalent variant of said CCP6 domain.

In an embodiment, said polypeptides are not the full-length C4BP alpha-chain. In an embodiment, the polypeptide comprising the CCP6 domain comprises a region of a protein different from C4BP. In a preferred embodiment, the polypeptide comprising the CCP6 domain does not comprise a region of a protein different from C4BP. In another embodiment, the polypeptide comprising the CCP6 domain of the C4BP alpha chain lacks at least the CCP1 domain, at least the CCP2 domain, at least the CCP3 domain, at least the CCP4 domain, at least the CCP5 domain, at least the CCP7 domain and/or at least the CCP8 domain of the C4BP alpha chain. In a still more preferred embodiment, the polypeptide comprising the CCP6 domain of the C4BP alpha chain does not contain any of the other CCP domains found in the C4BP alpha chain. Suitable polypeptides comprising the CCP6 domain of the C4BP alpha chain for use according to the present invention include, without limitation:

- a polypeptide comprising the CCP5, CCP6 and CCP7 domains of the C4BP alpha chain,
- a polypeptide comprising the CCP5, CCP6 and CCP7 domains of the C4BP alpha chain but lacking the one or more of any of the other CCP domains found in the C4BP alpha chain and, in particular, lacking CCP8 and
- a polypeptide comprising the CCP5, CCP6 and CCP7 domains of the C4BP alpha chain and wherein said polypeptide does not comprise a region of a protein different from C4BP.

The term "functionally equivalent variant", when referred to the polypeptide comprising the CCP6 domain of the C4BP alpha chain refers to any polypeptide having a sequence which derives from said polypeptide by insertion, deletion or substitution of one or more amino acids and which substantially preserves the functional activity of the original polypeptide. Suitable variants encompassed within the present invention include those polypeptides comprising a variant of the CCP6 domain showing at least 99%, at least 98%, at least 97%, at least 96%, at least 95%, at least 94%, at least 93%, at least 92%, at least 92%, at least 91%, at least 90%, at least 85%, at least 80%, at least 75%, at least 70%, at least 65%, at least 60% or less identity with the human CCP6 domain. Suitable methods for determining the identity of two polypeptides have been defined above in detail. In a preferred embodiment, the variant contains one or more of the cysteine residues substituted by serine. The expression "substantially preserves the functional activity of the original polypeptide", as used herein, refers to polypeptides which are capable of inhibiting the maturation of dendritic cells as determined, e.g., as shown in example 1 of the present invention or in the methods disclosed in international patent application WO2013/010998 A2.

Thus, a polypeptide is considered as a functionally equivalent to the C4BP isoform lacking β chain if it shows at least 100%, at least 95%, at least 90%, at least 85%, at least 80%, at least 75%, at least 70%, at least 65%, at least 60% or at least 50% of the activity of the C4BP isoform lacking 3 chain, in particular, the $\alpha_7\beta_0$ or the $\alpha_6\beta_0$ isoforms.

For example, the functionally equivalent variant of the polypeptide comprising the CCP6 domain of the C4BP alpha chain may be modified in order to modulate affinity for the receptor, modulate circulating half-life, modulate therapeutic half-life, modulate stability of the polypeptide, modulate cleavage by proteases, modulate dose, modulate release or bio-availability, facilitate purification, or improve or alter a particular route of administration. Similarly, the variants of the polypeptide comprising the CCP6 domain of the C4BP alpha chain may comprise protease cleavage sequences, reactive groups, antibody-binding domains (including but not limited to, FLAG or poly-His) or other affinity based sequences (including but not limited to, FLAG, poly-His, GST, etc.) or linked molecules (including but not limited to, biotin) that improve detection (including but not limited to, GFP), purification or other traits of the polypeptide.

In another embodiment, the functionally equivalent variant of the polypeptide comprising the CCP6 domain of the C4BP alpha chain is a fusion protein comprising a first region which comprises the CCP6 domain and a second region which comprises a polypeptide which does not form part of the C4BP alpha chain. The fusion protein of the present invention may comprise in an amino terminal to carboxy terminal direction, (a) the region which comprises the CCP6 domain and (b) the region which comprises a polypeptide which does not form part of the C4BP alpha chain. Alternatively, the fusion protein of the invention may comprise in an amino terminal to carboxy terminal direction, (a) the region which comprises a polypeptide which does not form part of the C4BP alpha chain and (b) the region which comprises the CCP6 domain. Preferably, the polypeptide forming part of the fusion protein and which comprises the CCP6 domain lacks at least the CCP1 domain, at least the CCP2 domain, at least the CCP3 domain, at least the CCP4 domain, at least the CCP5 domain, at least the CCP7 domain and/or at least the CCP8 domain of the C4BP alpha chain. In a still more preferred embodiment, the polypeptide comprising the CCP6 domain of the C4BP alpha chain does not contain any of the other CCP domains found in the C4BP alpha chain. Suitable polypeptides comprising the CCP6 domain of the C4BP alpha chain for use in the fusion protein according to the present invention include, without limitation:

- a polypeptide comprising the CCP5, CCP6 and CCP7 domains of the C4BP alpha chain,
- a polypeptide comprising the CCP5, CCP6 and CCP7 domains of the C4BP alpha chain but lacking the one or more of any of the other CCP domains found in the C4BP alpha chain and, in particular, lacking CCP8 and
- a polypeptide comprising the CCP5, CCP6 and CCP7 domains of the C4BP alpha chain and wherein said polypeptide does not comprise a region of a protein different from C4BP.

In a preferred embodiment, the polypeptide of the invention does not comprise a region of a protein different from C4BP. For example, the polypeptide of the invention cannot be a fusion protein comprising a region which forms part of a different protein from C4BP.

The functionally equivalent variants of CCP6 domain can also be fragments of the CCP6 domain of the C4BP alpha chain that substantially preserve the functional activity of the original polypeptide. Preferably are fragments of the CCP6 domain of the C4BP alpha chain wherein one or more of the cysteine residues are substituted by serine and substantially preserves the functional activity of the original peptide. Peptides having these features have been disclosed previously (WO2013/010998 A2).

In yet another aspect, the polypeptide comprising a functionally equivalent variant of the CCP6 domain of the C4BP alpha-chain is a polypeptide comprising a sequence selected from the group consisting of SEQ ID NO: 2, 3, 4 and 5 (see Table I).

TABLE 1

| Peptides derived from CCP6 domain | |
|---|---|
| Sequence | SEQ ID NO: |
| LSSPEPKL NNGEITQHRK SRPANHSVYF YG | 2 |
| HRK SRPANHSVYF YGDEISFSSH ETSRFSA | 3 |
| EISFSSH ETSRFSAISQ GDGTWSPRTP SSG | 4 |
| ITQHRK SRPANHSV | 5 |

In a preferred embodiment, the polypeptide of the invention consists on a sequence selected from the group consisting of SEQ ID NO: 2, 3, 4 and 5.

In a preferred embodiment, the sequence is SEQ ID NO: 5.

The functionally equivalent variants of said sequences SEQ ID NO: 2-5 are also contemplated by the present invention.

Functionally equivalent variants of the polypeptides comprising a sequence selected from the group consisting of SEQ ID NO: 2, SEQ ID NO: 3, SEQ ID N: 4 or SEQ ID NO: 5 include, without limitation, polypeptides modified by insertion, deletion or substitution of one or more amino acids of the polypeptides mentioned above as well as peptidomimetics thereof which maintain substantially the activity of said polypeptides. Methods adequate for determining whether a given polypeptide or peptide can be considered as a functionally equivalent variant of the isolated CCP6 polypeptide (SEQ ID NO: 1) or of the polypeptides of SEQ ID NO:2-5 include, e.g. the assays provided in example 8 of the international patent application WO2013/010998 A2 wherein a peptide is considered as a variant of the C4BP isoform lacking 3 chains if it shows an ability in generating tolerogenic dendritic cells when added to monocyte cells during the differentiation stage to immature dendritic cells and/or when added to immature dendritic cells during their maturation stage to mature dendritic cells. The ability of the variant to promote the generation of tolerogenic dendritic cells can be determined, e.g. by measuring the expression levels in the dendritic cells of maturation markers such as CD83, CD14 and/or CD1a of dendritic cells which have been matured in the presence of the variant (examples 1 and 2 of the international patent application WO2013/010998 A2). Thus, a peptide can be considered as a functionally equivalent to the C4BP isoform lacking 3 chain if it shows at least 100%, at least 95%, at least 90%, at least 85%, at least 80%, at least 75%, at least 70%, at least 65%, at least 60% or at least 50% of the activity of the C4BP isoform lacking β, in particular, the α7β0 or the α6β0.

Functionally equivalent variants of the isolated CCP6 polypeptide (SEQ ID NO: 1) or of the polypeptides of SEQ ID NO: 2-5 suitable for use in the present invention include, without limitation:

Peptides resulting from the derivatization of any of the above peptides including acylated, amidated, esterified derivatives and the like.

Peptides resulting from modification of any of the above peptides by substitutions (e.g., conservative amino acid substitutions) and/or insertions (e.g., small, single amino acid insertions, or insertions encompassing 2, 3, 4, 5, 10, 15, 20, or more contiguous amino acids) and/or deletions (e.g., small, single amino acid deletions, or deletions encompassing 2, 3, 4, 5, 10, 15, 20, or more contiguous amino acids). Thus, in certain embodiments, a variant of a native peptide sequence is one that differs from a naturally-occurring sequence by (i) one or more (e.g., 2, 3, 4, 5, 6, or more) conservative amino acid substitutions, (ii) deletion of 1 or more (e.g., 2, 3, 4, 5, 6, or more) amino acids, or (iii) a combination thereof. Deleted or inserted amino acids can be contiguous or non-contiguous.

In making such changes, the hydropathic index of amino acids is considered since it is known that certain amino acids may be substituted for other amino acids having a similar hydropathic index or score and result in a polypeptide with similar biological activity. For example, the relative hydropathic character of an amino acid residue affects the secondary and tertiary structure of the resultant polypeptide, which in turn defines the interaction of the polypeptide with other molecules, such as enzymes, substrates, receptors, antibodies, antigens, and the like. As outlined above, amino acid substitutions are generally based on the relative similarity of the amino acid side-chain substituents, for example, their hydrophobicity, hydrophilicity, charge, size, and the like. Exemplary substitutions which take various of the foregoing characteristics into consideration are well known to those of skill in the art and are set forth below in Table 2.

TABLE 2

Amino acid substitutions
Amino acid substitutions

| Original residue | Exemplary Residue Substitution | Original residue | Exemplary Residue Substitution |
|---|---|---|---|
| Ala | Gly;Ser | Ile | Leu;Val |
| Arg | Lys | Leu | Ile;Val |
| Asn | Gln;His | Lys | Arg |
| Asp | Glu | Met | Leu;Tyr |
| Cys | Ser | Ser | Thr |
| Gln | Asn | Thr | Ser |
| Glu | Asp | Trp | Tyr |
| Gly | Ala | Tyr | Trp |
| His | Asn;Gln | Val | Ile;Leu |

In a preferred embodiment, the peptides are modified by replacing one or more of the serine residues by cysteine.

Peptides having any of the above sequences but modified to include any of a variety of known chemical groups or molecules. Such modifications include, but are not limited to, glycosylation, acetylation, acylation, ADP-ribosylation, amidation, covalent attachment to polyethylene glycol (e.g., PEGylation), covalent attachment of flavin, covalent attachment of a heme moiety, covalent attachment of a nucleotide or nucleotide derivative, covalent attachment of a lipid or lipid derivative, covalent attachment of phosphatidylnositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, acylation, amidation, iodination, methylation, myristoylation. oxidation, proteolytic processing, phosphorylation, prenylation, racemization, selenoylation, sulfation, ubiquitination, modifications with fatty acids, transfer-RNA mediated addition of amino acids to proteins such as arginylation, etc. Analogues of an amino acid (including unnatural amino acids) and peptides with substituted linkages are also included.

Peptidomimetics of the above peptides. A "peptide mimetic" or "peptidomimetic" refers to various types or classes of molecules, as long as the resulting molecule mimics or resembles a desired polypeptide secondary (or localized tertiary) structural element. For example, a peptide mimetic is an oligomer that mimics peptide secondary structure through use of amide bond isosteres and/or modification of the native peptide backbone, including chain extension or heteroatom incorporation; examples of which include azapeptides, oligocarbamates, oligoureas, beta-peptides, gamma-peptides, oligo(phenylene ethynylene)s, vinylogous sulfonopeptides, poly-N-substituted glycines (peptoids) and the like. Methods for designing and synthesizing peptide mimetics are well known to one of skill in the art. In certain embodiments, it is contemplated that a peptide mimetic is used to overcome protease sensitivity, stabilize secondary structure and/or improve bioavailability relative to a naturally occurring CCP6 peptide analogues. In certain embodiments, a peptide mimetic of the invention is a reverse turn mimetic, e.g., a alpha-turn mimetic, a monocyclic beta-turn mimetic, a bicyclic beta-turn mimetic, a gamma-turn mimetic or a monocyclic gamma-turn mimetic.

The compounds disclosed above can be used in the prevention and/or treatment of an immunological disease caused by an undesired activation of the immune system.

The term "prevention", as used herein, refers to the administration of a compound of the invention in an initial or early stage of the disease, or to also prevent its onset.

The term "treatment" is used to designate the administration of a compound of the invention to control the progression of the disease before or after the clinical signs have appeared. Control of the progression of the disease is understood as the beneficial or desired clinical results which include but are not limited to reduction of the symptoms, reduction of the duration of the disease, stabilization of pathological conditions (specifically avoiding additional impairment), delaying the progression of the disease, improving the pathological condition and remission (both partial and complete). The control of the progression of the disease also involves a prolongation of survival in comparison to the expected survival if the treatment was not applied.

The expression "immunological disease caused by an undesired activation of the immune system" refers to any disease which is caused by an undesired activation of the immune system, including the innate or adaptative immune system as well as the humoral or cell branch of the immune system. Preferably, the immunological disease of the invention is a disease in which the immune system is activated in response to an alloantigen or an autoantigen. Therefore, immunological diseases in which the immune system is depressed are not encompassed by the present invention.

In a preferred embodiment, the immunological disease is selected from the group consisting of an immunoinflammatory disease, sepsis, autoimmune disease, transplant rejection, graft-versus-host disease and hypersensitivity diseases.

The term "immunoinflammatory disease", as used herein, refers to inflammatory diseases and disorders in which immune cells and/or cytokines are involved in the pathophysiology of the disease or disorder. Examples of immunoinflammatory diseases include conditions such as rheumatoid arthritis, juvenile rheumatoid arthritis, osteoarthritis, acute respiratory distress syndrome and asthma. The term immunoinflammatory disease includes both acute and chronic inflammatory disorders. The term "acute inflammatory disorder" is intended to include disorders and episodes of disorders, characterized by rapid onset of symptoms associated with an inflammatory response and relatively short duration of symptoms, whereas a "chronic inflammatory disorder" is intended to include disorders characterized by the continued presence of symptoms associated with an inflammatory response and ongoing duration of symptoms. Immunoinflammatory diseases which can be treated with the methods according to the present invention include, without limitation, cardiovascular diseases such as infarct or stroke, atherosclerosis, pulmonary fibrosis, rheumatoid arthritis, juvenile rheumatoid arthritis, osteoarthritis, acute respiratory distress syndrome, asthma, and cancer. Also comprised within the immunoinflammatory diseases that can be treated according to the present invention are diseases which appear during pregnancy such as pre-eclampsia and eclampsia. Pre-eclampsia is a pregnancy-related disease characterised by hypertension, proteinuria and oedema. Pre-eclampsia is understood and shall be defined herein to encompass and reside within a spectrum of pre-eclampsia disorders, including placental insufficiency, intrauterine growth retardation, early miscarriage, preterm birth, intrauterine death and eclampsia.

The term "sepsis", as used herein, refers to a systemic host response to microorganisms in previously sterile tissues characterized by end-organ dysfunction away from the primary site of infection. To qualify as sepsis, there must be an infection suspected or proven (by culture, stain, or polymerase chain reaction (PCR)), or a clinical syndrome pathognomonic for infection. Specific evidence for infection includes WBCs in normally sterile fluid (such as urine or cerebrospinal fluid (CSF), evidence of a perforated viscus (free air on abdominal x-ray or CT scan, signs of acute peritonitis), abnormal chest x-ray (CXR) consistent with pneumonia (with focal opacification), or petechiae, purpura, or purpura fulminans. The more critical subsets of sepsis are severe sepsis (sepsis with acute organ dysfunction) and septic shock (sepsis with refractory arterial hypotension). As an alternative, when two or more of the systemic inflammatory response syndrome criteria are met without evidence of infection, patients may be diagnosed simply with "SIRS." Patients with SIRS and acute organ dysfunction may be termed "severe SIRS." Patients are defined as having "severe sepsis" if they have sepsis plus signs of systemic hypoperfusion: either end-organ dysfunction or serum lactate greater than 4 mmol/dL. Other signs include oliguria and altered mental status. Patients are defined as having septic shock if they have sepsis plus hypotension after aggressive fluid resuscitation (typically upwards of 6 liters or 40 ml/kg of crystalloid). Examples of end-organ dysfunction include acute lung injury or acute respiratory distress syndrome, encephalopathy, or dysfunction affecting liver (disruption of protein synthetic function and metabolic functions), kidney (oliguria and anuria, electrolyte abnormalities, volume overload), and heart (systolic and diastolic heart failure).

Suitable sepsis conditions that can be treated with the compounds according to the present invention include, without limitation, severe sepsis and septic shock. In one embodiment, the condition associated with sepsis syndrome is selected from the group consisting of an organ dysfunction, preferably a kidney dysfunction or a liver dysfunction, a multiple organ dysfunction syndrome (MODS), an acute respiratory distress syndrome (ARDS), and disseminated intravascular coagulation (DIC).

Sepsis may be induced by a bacterium or more than one bacterium selected from the group consisting of Gram-negative bacteria and Gram-positive bacteria. Preferably, the Gram-negative bacterium is selected from the group consisting of *Escherichia coli, Klebsiella species, Serratia species, Enterobacter species, Proteus species, Pseudomonas aeruginosa, Haemophilus influenzae, Neisseria species*, and *Listeria* species. Alternatively, the Gram-positive bacterium is selected from the group consisting of *Staphylococcus aureus, Streptococcus pneumoniae*, coagulase-negative Staphylococci, *Enterococcus* species, *Streptococcus pyogenes*, and *Streptococcus viridans*. In one embodiment, the sepsis syndrome is induced by LPS. In yet another embodiment, the sepsis is induced by a microorganism or more than one microorganism selected from the group consisting of anaerobic bacteria, fungi, rickettsiae, chlamydiae, mycoplasma, spirochetes, and viruses.

In a preferred embodiment, the immunological disease is an autoimmune disease.

The term "autoimmune disease", "disease associated with immune dysfunction/dysregulation" or "immune inflammatory disease" is used throughout the specification to refer to a pathogenic condition in which the patients immune system results in disease from a self antigen (autoimmunity) or a foreign antigen (immune dysfunction/dysregulation or immune inflammatory disease). Autoimmunity is present in everyone to some extent. It is usually harmless and probably a universal phenomenon of vertebrate life. However, autoimmunity can be the cause of a broad spectrum of human illnesses, known as autoimmune diseases. This concept of autoimmunity as the cause of human illness is relatively new, and it was not accepted into the mainstream of medical thinking until the 1950s and 1960s. Autoimmune diseases are, thus, defined when the progression from benign autoimmunity to pathogenic autoimmunity occurs. This progression is determined by both genetic influences and environmental triggers. The concept of autoimmunity as the actual cause of human illness (rather than a consequence or harmless accompaniment) can be used to establish criteria that define a disease as an autoimmune disease. Autoimmune diseases or diseases which are characterized as involving immune dysfunction or disregulation (immune inflammatory disease), which may be treated by the present invention include systemic lupus erythematosus (SLE), lupus nephritis, central nervous system (CNS) lupus, diabetes mellitus (type I), asthma, ulcerative colitis, Crohn's disease, Grave's disease, arthritis, including rheumatoid arthritis and osteoarthritis, pernicious anemia, and multiple sclerosis, among numerous others. Numerous autoimmune diseases may be treated using the method of the present invention including autoimmune blood diseases, including pernicious anemia, autoimmune hemolytic anemia, aplastic anemia, idiopathic thrombocytopenic purpura, ankylosing spondilitis; autoimmune diseases of the musculature including polymyositis and dermatomyositis, autoimmune diseases of the ear including autoimmune hearing loss and Meniere's syndrome, autoimmune eye diseases, including Mooren's disease, Reiter's syndrome and Vogt-Koyanagi-Harada disease, autoimmune diseases of the kidney including glomerulonephritis, IgA nephropathy, and lupus nephritis; diabetes mellitus (type I); autoimmune skin diseases including pemphigus (autoimmune bullous diseases), such as pemphigus vulgaris, pemphigus fbliaceus, pemphigus erythematosus, bullous pemphigoid, vitiligo, epidermolysis bullosa acquisita, psoriasis and alopecia areata; cardiovascular autoimmune diseases, including autoimmune myocarditis, vasculitis including Churg-Strauss syndrome, giant cells arteritis, Kawasaki's disease, polyarteritis nodosa, Takayasu's arteritis and Wegener's granulomatosis; endocrine autoimmune diseases, including Addison's disease, autoimmune hypoparathyroidism, autoimmune hypophysitis, autoimmune oophoritis, autoimmune orchitis, Grave's Disease, Hashimoto's thyroiditis, polyglandular autoimmune syndrome type 1 (PAS-I) polyglandular autoimmune syndrome type 2 (PAS-2), and polyglandular autoimmune syndrome type 3 (PAS-3); autoimmune gastroenteric diseases including autoimmune hepatitis, primary biliary cirrhosis, inflammatory bowel disease, celiac disease, Crohn's disease; autoimmune nervous diseases, including multiple sclerosis, myasthenia gravis, Guillan-Barre syndrome and chronic inflammatory demyelinating neuropathy; and systemic autoimmune diseases including systemic lupus erythematosus, antiphospholid syndrome, autoimmune lymphoproliferative disease, autoimmune polyendocrinopathy, Bechet's disease, Goodpasture's disease, arthrtitis, including rheumatoid arthritis, osteoarthritis and septic arthritis, sarcoidosis, scleroderma and Sjogren's syndrome and psoriasis among others.

In an embodiment, the autoimmune disease is lupus erythematosus. The expression "lupus erythematosus", as used herein, refers to a name given to a collection of autoimmune diseases that have common symptoms that affect joints, skin, kidneys, blood cells, heart and lungs. Lupus erythematosus may manifest as systemic disease or in a purely cutaneous form also known as incomplete lupus erythematosus. Lupus has four main types: systemic, discoid, drug-induced and neonatal. The term "lupus erythematosus" in the context of the present invention encompasses, without limitation, acute cutaneous lupus erythematosus, subacute cutaneous lupus erythematosus, discoid lupus erythematosus (chronic cutaneous), childhood discoid lupus erythematosus, generalized discoid lupus erythematosus, localized discoid lupus erythematosus, chilblain lupus erythematosus (Hutchinson), lupus erythematosus-lichen planus overlap syndrome, lupus erythematosus panniculitis (lupus erythematosus profundus), tumid lupus erythematosus, verrucous lupus erythematosus (hypertrophic lupus erythematosus), cutaneous lupus mucinosis, complement deficiency syndromes, drug-induced lupus erythematosus, neonatal lupus erythematosus and systemic lupus erythematosus. The most common severe form is systemic lupus erythematosus.

In a preferred embodiment, the autoimmune disease is selected from the group consisting of systemic lupus erythematosus, lupus nephritis, rheumatoid arthritis and ulcerative colitis; more preferably is selected from the group consisting of systemic lupus erythematosus, lupus nephritis and rheumatoid arthritis. In a preferred embodiment, the autoimmune disease is selected from the group consisting of systemic lupus erithematosus and lupus nephritis. In a preferred embodiment the autoimmune disease is systemic lupus erythematosus.

In another preferred embodiment, the autoimmune disease is rheumatoid arthritis.

The expression "systemic lupus erythematosus" or "SLE", as used herein, refers to a systemic autoimmune disease in which the body's immune system mistakenly attacks healthy tissue in many parts of the body. Symptoms vary from person to person and may be mild to severe. Common symptoms include painful and swollen joints, fever, chest pain, hair loss, mouth ulcers, swollen lymph nodes, feeling tired, and a red rash which is most commonly on the face. Often there are periods of illness, called flares, and periods of remission when there are few symptoms. Almost everyone with SLE has joint pain and swelling. Some develop arthritis. SLE often affects the joints of the fingers, hands, wrists, and knees. Renal disease in SLE carries significant morbidity and mortality. Acute or chronic renal impairment may develop with lupus nephritis, leading to acute or end-stage kidney failure.

The expression "lupus nephritis" or "LN", also known as SLE nephritis, is an inflammation of the kidneys caused by systemic lupus erythematosus. It is a type ofglomerulonephritis in which the glomeruli become inflamed. As the result of SLE, the cause of glomerulonephritis is said to be secondary and has a different pattern and outcome from conditions with a primary cause originating in the kidney. General symptoms of lupus nephritis include fever, edema, high blood pressure, joint pain, muscle pain, malar rash and foamy urine.

The expression "rheumatoid arthritis" or "RA", as used herein, refers to a long-term systemic autoimmune disorder characterized by chronic inflammation of the joints and the subsequent destruction of cartilage and bone. It typically results in warm, swollen, and painful joints. Pain and stiffness often worsen following rest. Most commonly, the wrist and hands are involved, with the same joints typically involved on both sides of the body. The disease may also affect other parts of the body. This may result in a low red blood cell count, inflammation around the lungs, and inflammation around the heart. Fever and low energy may also be present. Often, symptoms come on gradually over weeks to months. RA primarily starts as a state of persistent cellular activation leading to autoimmunity and immune complexes in both joints and other organs where it manifests. The initial site of disease is the synovial membrane, where swelling and congestion leads to infiltration by immune cells. The various phases of progression of RA are:

Initiation phase, due to non-specific inflammation.

Amplification phase, due to T cell activation

Chronic inflammatory phase with tissue injury, due to cytokines IL-1, TNF-alpha and IL-6.

The expression "transplant rejection", as used herein, refers to an immune condition in which a transplanted cell, tissue, or organ is not accepted by the body of the transplant recipient. The expression transplant rejection encompasses both acute and chronic transplant rejection.

"Acute rejection or AR" is the rejection by the immune system of a tissue transplant recipient when the transplanted tissue is immunologically foreign. Acute rejection is characterized by infiltration of the transplanted tissue by immune cells of the recipient, which carry out their effector function and destroy the transplanted tissue. The onset of acute rejection is rapid and generally occurs in humans within a few weeks after transplant surgery.

"Chronic transplant rejection or CR" generally occurs in humans within several months to years after engraftment, even in the presence of successful immunosuppression of acute rejection. Fibrosis is a common factor in chronic rejection of all types of organ transplants. Chronic rejection can typically be described by a range of specific disorders that are characteristic of the particular organ. For example, in lung transplants, such disorders include fibroproliferative destruction of the airway (bronchiolitis obliterans); in heart transplants or transplants of cardiac tissue, such as valve replacements, such disorders include fibrotic atherosclerosis; in kidney transplants, such disorders include, obstructive nephropathy, nephrosclerosis, tubulointerstitial nephropathy; and in liver transplants, such disorders include disappearing bile duct syndrome. Chronic rejection can also be characterized by ischemic insult, denervation of the transplanted tissue, hyperlipidemia and hypertension associated with immunosuppressive drugs.

As is known in the transplantation field, the transplant organ, tissue or cell(s) may be allogeneic or xenogeneic, such that the grafts may be allografts or xenografts. A feature of the graft tolerant phenotype detected or identified by the subject methods is that it is a phenotype which occurs without immunosuppressive therapy, i.e., it is present in a host that is not undergoing immunosuppressive therapy such that immunosuppressive agents are not being administered to the host. The transplant graft maybe any solid organ and skin transplant. Examples of organ transplants that can be treated with the methods described herein include but are not limited to kidney transplant, pancreas transplant, liver transplant, heart transplant, lung transplant, intestine transplant, pancreas after kidney transplant, and simultaneous pancreas-kidney transplant.

The methods according to the present invention are also suitable for the prevention and/or treatment of delayed Graft Function (DGF) due to ischemia-reperfusion injury. The term "delayed graft function", as used herein, refers to a form of acute renal failure resulting in post-transplantation oliguria, increased allograft immunogenicity and risk of acute rejection episodes, and decreased long-term survival. DGF may be caused by different factors related to the donor and prerenal, renal, or postrenal transplant factors related to the recipient. However, a major cause of delayed graft function is ischaemia and reinstitution of blood flow in ischaemically damaged kidneys after hypothermic preservation.

The term "graft-versus-host disease" or GVHD, as used herein, refers to a condition that occurs when T cells present in donor tissue attack the host, or recipient, of the grafted cells or tissue. Any type of GVHD can be treated by the therapeutic agents of the present invention, including acute GVHD and chronic GVHD.

The term "hypersensitivity disease" refers to a condition in which the subject has an abnormal sensitivity to an innocuous agent, known as allergen. Hypersensivity disease can be categorized into four types, Type I, Type II, Type III and Type IV. Type I is described as atopic or anaphylactic which results from a release of mediators from IgE-sensitized basophils and mast cells. Type II is described as cytotoxic which involves complement-fixing antibody with cell lysis or antibody-dependent cellular cytotoxicity. Type III is described as immune-complex-mediated which is associated with soluble antigen-antibody complexes. Type IV is described as cell-mediated or delayed hypersensitivity which results from a release of lymphokines by sensitized T lymphocytes after contact with an antigen.

In a preferred embodiment, the immunological disease is inflammatory bowel disease, more preferably ulcerative colitis. In another embodiment, the immunological disease is Crohn's disease.

In the first aspect of the invention the compound is administered subcutaneously. The term "subcutaneously", as used herein, refers to a route of administration by subcutaneous injection, wherein the compound is administered as a bolus into the subcutis, the layer of skin directly below the dermis and epidermis. Methods for administering a compound subcutaneously are well known by the person skilled in the art.

In the first aspect of the invention the compound is administered in a regimen comprising a plurality of administrations (i.e. at least two administrations). In a preferred embodiment, the regimen comprises at least 2 administrations, at least 3, at least 4, at least 5, at least 6, at least 7, at least 8, at least 9, at least 10, at least 11, at least 12, at least 13, at least 14, at least 15, at least 30, at least 50, at least 100 or more. Preferably, the compound is administered chronically. Preferably, the compound is administered at least during 1 year, at least during 2 years, at least during 5 years or more.

In the first aspect of the invention the compound is administered no more than once a week. The expression "the compound is administered no more than once a week" means that during a week the maximum number of administrations is one. This means that if the compound is administered on day 1, the subsequent administration cannot be on days 2, 3, 4, 5, 6 or 7. However, the expression "the compound is administered no more than once a week" encompasses the possibility that no administration is given during a week, for example, because the compound is administered once every two weeks. Therefore, according to the invention one administration is separated at least 7 days from another administration. Therefore, in a preferred embodiment, each administration is separated at least by 7 days from another, at least by 8 days, at least by 9 days, at least by 10 days, at least by 11 days, at least by 12 days, at least by 13 days, at least by 14 days, at least by 15 days, at least by 16 days, at least by 17 days, at least by 18 days, at least by 19 days, at least by 20 days, at least by 21 days, at least by 22 days, at least by 23 days, at least by 24 days, at least by 25 days, at least by 26 days, at least by 27 days, at least by 28 days, at least by 29 days, at least by 30 days, at least by 31 days, at least by 32 days, at least by 33 days, at least by 34 days, at least by 35 days, at least by 36 days, at least by 37 days, at least by 38 days, at least by 39 days, at least by 40 days, at least by 41 days, at least by 42 days, at least by 43 days, at least by 44 days, at least by 45 days, at least by 46 days, at least by 47 days, at least by 48 days, at least by 49 days, at least by 50 days, at least by 51 days, at least by 52 days, at least by 53 days, at least by 54 days, at least by 55 days, at least by 56 days, at least by 57 days, at least by 58 days, at least by 59 days, at least by 60 days or more.

In a preferred embodiment, the compound is administered once a week. In another preferred embodiment, the compound is administered once every two weeks. In another embodiment, the compound is administered once every three weeks. In another embodiment, the compound is administered once every four weeks. In another embodiment, the compound is administered once every five weeks. In another embodiment, the compound is administered once every six weeks. In another embodiment, the compound is administered once every seven weeks. In another embodiment, the compound is administered once every eight weeks.

In another embodiment, the compound is administered once every nine weeks. In another embodiment, the compound is administered once every ten weeks. In another embodiment, the compound is administered once every eleven weeks. In another embodiment, the compound is administered once every twelve weeks. In an embodiment, the compound is administered monthly. In another embodiment, the compound is administered once every two months.

The dose of the composition for treating an immunological disease or disorder may be determined according to parameters understood by a person skilled in the medical art. Accordingly, the appropriate dose may depend upon the patient's (e.g., human) condition, that is, stage of the disease, general health status, as well as age, gender, and weight, and other factors familiar to a person skilled in the medical art.

The compound of the invention has efficacy at low doses. Therefore, in a preferred embodiment, the dose of each administration ranges from 0.24 $mg/m^2$ to 9.99 $mg/m^2$. In a more preferred embodiment, the dose of each administration ranges from 0.24 $mg/m^2$ to 5 $mg/m^2$, preferably from 0.3 $mg/m^2$ to 4.5 $mg/m^2$, preferably from 0.4 $mg/m^2$ to 4.3 $mg/m^2$, even more preferably from 0.42 $mg/m^2$ to 4.26 $mg/m^2$. In a preferred embodiment, the dose is 0.42 $mg/m^2$. In another preferred embodiment, the dose is 4.26 $mg/m^2$.

In an embodiment the dose of each administration ranges from 4 $mg/m^2$ to 9.99 $mg/m^2$, preferably from 5 $mg/m^2$ to 8 $mg/m^2$, preferably from 6 $mg/m^2$ to 8 $mg/m^2$, preferably from 7 $mg/m^2$ to 8 $mg/m^2$.

In an embodiment the dose of each administration ranges from 1 $mg/m^2$ to 9 $mg/m^2$, preferably from 2 $mg/m^2$ to 8 $mg/m^2$, preferably from 3 $mg/m^2$ to 7 $mg/m^2$, more preferably from 4 $mg/m^2$ to 6 $mg/m^2$.

In another embodiment, the compound is administered at a dose of from 0.24 $\mu g/m^2$ to 0.24 $mg/m^2$, preferably from 1 $\mu g/m^2$ to 0.24 $mg/m^2$, preferably from 10 $\mu g/m^2$ to 0.24 $mg/m^2$, preferably from 50 $\mu g/m^2$ to 0.24 $mg/m^2$, more preferably from 100 $\mu g/m^2$ to 0.24 $mg/m^2$, more preferably from 150 $\mu g/m^2$ to 0.24 $mg/m^2$, more preferably from 200 $\mu g/m^2$ to 0.24 $mg/m^2$.

A subject in need of such treatment may be a human or may be a non-human primate or other animal (i.e., veterinary use) who has developed symptoms of an immunological disease or who is at risk for developing an immunological disease. Examples of non-human primates and other animals include but are not limited to farm animals, pets, and zoo animals (e.g., horses, cows, buffalo, llamas, goats, rabbits, cats, dogs, chimpanzees, orangutans, gorillas, monkeys, elephants, bears, large cats, etc.). In a preferred embodiment, the compound is administered to a mammal, preferably a human.

As used herein, a patient (or subject) may be any mammal, including a human, that may have or be afflicted with an immunological disease or disorder, or that may be free of detectable disease. Accordingly, the treatment may be administered to a subject who has an existing disease, or the treatment may be prophylactic, administered to a subject who is at risk for developing the disease or condition.

The treatment of the invention may also comprise a previous step of administration that does not need to be separated by seven days from the subsequent administration. In a particular case this could be considered an induction step. Therefore, in an embodiment the administration further comprises a previous step of subcutaneous administration of the compound separated by less than seven days from the subsequent administration. Preferably, the previous step is separated by less than 6 days from the subsequent administration, more preferably by less than 5 days, more preferably by less than 4 days, more preferably by less than 3 days, more preferably by less than 2 days, preferably by less than 1 day.

In a more preferred embodiment the previous step of subcutaneous administration is separated by two days from the subsequent step. Preferably, the previous step of a treatment for rheumatoid arthritis is separated by less than three days from the subsequent step, preferably by two days, preferably by less than two days, preferably by one day, preferably by less than one day.

In a preferred embodiment, the dose administered at the previous step and the dose administered in each subsequent administration is the same.

In another preferred embodiment, the dose administered at the previous step is higher than the dose administered in each subsequent administration. In a preferred embodiment, said dose is comprised between 40-45 $mg/m^2$, preferably is of 42.84 $mg/m^2$. Preferably, said dose is administered in the treatment of rheumatoid arthritis. In another preferred embodiment, said dose is administered in the treatment of systemic lupus erythematosus or lupus nephritis.

In an embodiment, the medicament comprises the compound of the invention as sole therapeutic agent.

In another embodiment, the compound is administered in combination with one or more therapeutic agents useful in the treatment of an immunological disease caused by an undesired activation of the immune system.

The expression "in combination", as used herein, has to be understood that the compound of the invention can be administered together or separately, simultaneously, concurrently or sequentially with a therapeutic agent useful in the treatment of an immunological disease caused by an undesired activation of the immune system in any order, e.g. the administration of the compound can be made first, followed by the administration of one or more therapeutic agent(s) useful in the treatment of the disease; or the administration of the compound of the invention can be made last, preceded by the administration of one or more therapeutic agent(s) useful in the treatment of the disease; or the administration of the compound of the invention can be made concomitantly with one or more therapeutic agent(s) useful in the treatment of the disease.

A person skilled in the art understands that the medicament for combined administration of the compound of the invention and an additional therapeutic agent useful in the treatment of an immunological disease can be in the form of a single dosage form or in separate dosage forms.

The expression "therapeutic agent useful in the treatment of an immunological disease caused by an undesired activation of the immune system", as used herein, refers to an agent suitable to be used to treat one of the diseases mentioned above.

In a preferred embodiment, the therapeutic agent for treating systemic lupus erythematosus, preferably lupus nephritis, is selected from the group consisting of cyclophosphamide, mycophenolate mofetil, calcineurin inhibitors, rituximab, ocrelizumab, belimumab, atacicept, abatacept, alemtuzumab, sirukumab, tocilizumab, etanercept, eculizumab, epratuzumab, abetimus/LJP-394, BG9588/IDEC 131, intravenous immunoglobulins, hydroxychloroquine, tacrolimus and corticoids.

In a preferred embodiment, the therapeutic agent for treating rheumatoid arthritis is selected from the group consisting of infliximab, adalimumab, certolizumab, golimumab and etanercept.

In a preferred embodiment, the therapeutic agent for treating inflammatory bowel disease is selected from the group consisting of cyclosporine A, tacrolimus, methotrexate, thiopurines and anti-TNF agents.

Therapeutic agents for the treatment of autoimmune diseases, particularly autoimmune renal diseases, more particularly lupus nephritis can be selected from the group consisting of immunosuppressors, esteroids, vitamin D, VIP (vasoactive intestinal peptide), hydroxychloroquine, chloroquine and T cell vaccination.

In an embodiment, the immunosuppressors are selected from the group consisting of cyclophosphamide, mycophenolate mofetil, azathioprine and anticalcineurinics.

In an embodiment, the steroids are selected from the group consisting of prednisolone and methylprednisolone.

Therapeutic agents for the treatment of autoimmune diseases, particularly autoimmune renal disease, more particularly lupus nephritis can be compounds targeting a target selected from the group consisting of T cells, B cells, co-stimulation inhibition, inflammatory cytokines, cell adhesion molecules and complement components.

In an embodiment the T cell target can be selected from the group consisting of CD3, CD52, IL-2 and LFA-1. Preferably, the compounds that target T cells are selected from the group consisting of OKT3, alemtuzumab, basilximab, efalizumab, laquinimod and rapamycin.

In an embodiment the B cell target can be selected from the group consisting of CD20, CD22, BAFF, BAFF and APRIL, FcγRIIb and CD74. Preferably, the compounds that target B cells are selected from the group consisting of rituximab, ocrelizumab, oftumumab, veltuzumab, obinutuzumab, epratuzumab, belimumab, blisibimod, atacicept, soluble FcγRIIb, milatuzumab and tabalumab.

In an embodiment the co-stimulation inhibition can be selected from the group consisting of CD40 and CD80/86. Preferably, the compounds that target co-stimulation inhibition are selected from the group consisting of ASKP1240, abatacept and, belatacept.

In an embodiment, the inflammatory cytokines target can be selected from the group consisting of IL-1β, IL-6, IL-6R, TNF, TWEAK, IFNα, IL-17A, IL-12/IL-23, IFNγ, MIF and IL-5. Preferably, the compounds that target inflammatory cytokines are selected from the group consisting of canakinumab, anakinra, sirukumab, tocilizumab, etanercept, infliximab, adalimumab, golimumab, certolizumab, BIIB023, sifalimumab, rontalizumab, secukinumab, ustekinumab, AMG 811, imalumab, mepolizumab, brodalumab, briakinumab, sarilumab, rilonacept and anifrolumab.

In an embodiment, the cell adhesion molecules target is VLA-1. Preferably, the compound that targets cell adhesion molecules is natalizumab.

In an embodiment, the complement component target is selected from the group consisting of C5 and C5aR. Preferably, the compounds that target complement components are selected from the group consisting of eculizumab, mubodina, LFG316 and CCX168.

Table 3 shows the different compounds mentioned above and their target.

TABLE 3

Compounds for the treatment of autoimmune diseases. Adapted from Holdsworth S.R. et al. 2016. Nat. Rev. 12:217-231.

| Target | | Compound |
|---|---|---|
| T cells | CD3 | OKT3 |
| | CD52 | alemtuzumab |
| | IL-2 | Basilximab |
| | | rapamycin |
| | LFA-1 | efalizumab |
| B cells | CD20 | rituximab |
| | | ocrelizumab |
| | | oflumumab |
| | | veltuzumab |
| | | obinutuzumab |
| | CD22 | epratuzumab |
| | BAFF | belimumab |
| | | blisibimod |
| | | tabalumab |
| | BAFF and APRIL | atacicept |
| | FCγRIIb | soluble FCγRIIb |
| | CD74 | milatuzumab |
| Co-stimulation inhibition | CD40 | ASKP1240 |
| | CD80/86 | abatacept |
| | | belatacept |
| Inflammatory cytokines | IL-1β | canakinumab |
| | | anakinra |
| | | rilonacept |
| | IL-6 | sirukumab |
| | IL-6R | to cilizumab |
| | | sarilumab |
| | TNF | etanercept |
| | | infliximab |
| | | adalimumab |
| | | golimumab |
| | | certolizumab |
| | TWEAK | BIIB023 |
| | IFNα | sifalimumab |
| | | rontalizumab |
| | | anifrolumab |
| | IL-17A | secukinumab |
| | | brodalumab |
| | IL-12/IL-23 | ustekinumab |
| | | briakinumab |
| | IFNγ | AMG 811 |
| | MIF | imalumab |
| | IL-5 | mepolizumab |
| Cell adhesion molecules | VLA-1 | natalizumab |
| Complement components | C5 | eculizumab |
| | | mubodina |
| | | LFG316 |
| | C5aR | CCX168 |

In a preferred embodiment, the therapeutic agent useful in the treatment of an immunological disease caused by an undesired activation of the immune system is selected from the group consisting of cyclosporine A, tacrolimus, methotrexate, thiopurines, anti-TNF agents, infliximab, adalimumab, certolizumab, golimumab, etanercept, rituximab, epratuzumab, belimumab, rapamycin, anti-interferon antibodies, tocilizumab, laquinimod, tabalumab, ofatumumab, ixekizumab, brodalumab, briakinumab, sarilumab, rilonacept, anifrolumab, cyclophosphamide, mycophenolate mofetil, azathioprine, anticalcineurinics, prednisolone, methylprednisolone, vitamin D, vasoactive intestinal peptide, hydroxychloroquine, chloroquine, ocrelizumab, atacicept, abatacept, alemtuzumab, sirukumab, eculizumab and T cell vaccine.

Therapeutic Uses of C4BP Isoforms Lacking Beta Chain and Polypeptides Comprising CCP6 Domain of the Alpha Chain of C4BP at Low Doses The authors have demonstrated that, surprisingly, 50 μg of rC4BP(β−) administered subcutaneously once every two weeks have higher therapeutic effect than when the same dose is administered intraperitoneally following the same regimen. The same surprising effect is obtained when the dose administered is 5 μg (FIG. 5). Survival was also higher when the doses of 5 μg and 50 μg were administered by subcutaneous route when compared with intraperitoneal route (FIG. 6).

In a second aspect, the invention relates to a compound selected from the group consisting of:

a) a C4BP isoform lacking the beta chain wherein if at least one of the alpha-chains forming said isoform is a deletion mutant which lacks at least one of the CCP domains, the CCP6 domain is preserved in said alpha-chain;

b) a polypeptide comprising a full-length C4BP alpha-chain or a deletion mutant thereof that preserves the CCP6 domain; and c) a polypeptide comprising the CCP6 domain of the C4BP alpha-chain or a functionally equivalent variant of said CCP6 domain for use in the prevention and/or treatment of an immunological disease caused by an undesired activation of the immune system, wherein the compound is administered subcutaneously at a dose of from 0.24 mg/m2 to 9.99 mg/m2.

In a further aspect, the invention relates to the use of a compound selected from the group consisting of:

a) a C4BP isoform lacking the beta chain wherein if at least one of the alpha-chains forming said isoform is a deletion mutant which lacks at least one of the CCP domains, the CCP6 domain is preserved in said alpha-chain;

b) a polypeptide comprising a full-length C4BP alpha-chain or a deletion mutant thereof that preserves the CCP6 domain; and c) a polypeptide comprising the CCP6 domain of the C4BP alpha-chain or a functionally equivalent variant of said CCP6 domain for the manufacture of a medicament for the prevention and/or treatment of an immunological disease caused by an undesired activation of the immune system, wherein the compound is administered subcutaneously at a dose of from 0.24 mg/$m^2$ to 9.99 mg/m2.

In a further aspect, the invention relates to a method for the prevention and/or treatment of an immunological disease caused by an undesired activation of the immune system in a subject in need thereof comprising the administration to said subject of a compound selected from the group consisting of:

a) a C4BP isoform lacking the beta chain wherein if at least one of the alpha-chains forming said isoform is a deletion mutant which lacks at least one of the CCP domains, the CCP6 domain is preserved in said alpha-chain;

b) a polypeptide comprising a full-length C4BP alpha-chain or a deletion mutant thereof that preserves the CCP6 domain; and c) a polypeptide comprising the CCP6 domain of the C4BP alpha-chain or a functionally equivalent variant of said CCP6 domain.

All the embodiments disclosed in regards to the first aspect of the invention are applicable to the second aspect of the invention.

Doses of the compounds of the invention may be expressed either in mg of isoform or polypeptide per kg of body weight or in mg of isoform or polypeptide per square meter of body surface. The article from Reagan-Shaw S. et al. (Reagan-Shaw S. et al. "*Dose translation from animal to human studies revisited*". FASEB J 2008, 22(3):659-661) provides the standard conversion factors used to convert mg/kg to mg/$m^2$.

$$\text{Dose(mg/kg)} \times K_m = \text{Dose(mg/m}^2\text{)}$$

The article also explains that this conversion is the basis for converting dose in a first animal species to dose in a second animal species (allometric dose translation). Thus, animal dose (AD) in mg/kg can be converted to human equivalent dose (HED) in mg/kg using the following formula:

$$HED \text{ (mg/kg)} = AD \text{ (mg/kg)} \times \frac{\text{Animal } K_m}{\text{Human } K_m}$$

wherein the $K_m$ for each species is shown in Table 4 (data extracted from Reagan-Shaw S. et al. "*Dose translation from animal to human studies revisited*". FASEB J 2008, 22(3): 659-661).

TABLE 4

$K_m$ factor for conversion of AD to HED

| Species | | $K_m$ factor |
|---|---|---|
| Human | Adult | 37 |
| | Child | 25 |
| Baboon | | 20 |
| Dog | | 20 |
| Monkey | | 12 |
| Rabbit | | 12 |
| Guinea pig | | 8 |
| Rat | | 6 |
| Hamster | | 5 |
| Mouse | | 3 |

Thus, the experiments with doses of 5 μg and 50 μg in mice correspond to general doses in mammals of 0.42 mg/$m^2$ and 4.26 mg/$m^2$.

The compound of the invention has efficacy at low doses. Therefore, in a preferred embodiment, the dose of each administration ranges from 0.24 mg/$m^2$ to 9.99 mg/$m^2$. In a more preferred embodiment, the dose of each administration ranges from 0.24 mg/$m^2$ to 5 mg/$m^2$, preferably from 0.3 mg/$m^2$ to 4.5 mg/$m^2$, preferably from 0.4 mg/$m^2$ to 4.3 mg/$m^2$, even more preferably from 0.42 mg/$m^2$ to 4.26 mg/$m^2$. In a preferred embodiment, the dose is 0.42 mg/$m^2$. In another preferred embodiment, the dose is 4.26 mg/$m^2$.

In an embodiment the dose of each administration ranges from 4 mg/$m^2$ to 9.99 mg/$m^2$, preferably from 5 mg/$m^2$ to 8 mg/$m^2$, preferably from 6 mg/$m^2$ to 8 mg/$m^2$, preferably from 7 mg/$m^2$ to 8 mg/$m^2$.

In an embodiment the dose of each administration ranges from 1 mg/$m^2$ to 9 mg/$m^2$, preferably from 2 mg/$m^2$ to 8 mg/$m^2$, preferably from 3 mg/$m^2$ to 7 mg/$m^2$, more preferably from 4 mg/$m^2$ to 6 mg/$m^2$.

Pharmaceutical Compositions of the Invention and Uses Thereof

In a third aspect, the invention relates to a pharmaceutical composition comprising from 0.45 mg to 18.90 mg of a compound selected from the group consisting of:

(a) a C4BP isoform lacking the beta chain wherein if at least one of the alpha-chains forming said isoform is a deletion mutant which lacks at least one of the CCP domains, the CCP6 domain is preserved in said alpha-chain;

(b) a polypeptide comprising a full-length C4BP alpha-chain or a deletion mutant thereof that preserves the CCP6 domain; and (c) a polypeptide comprising the CCP6 domain of the C4BP alpha-chain or a functionally equivalent variant of said CCP6 domain and a pharmaceutically acceptable excipient suitable for subcutaneous administration for use in the prevention and/or treatment of an immunological disease caused by an undesired activation of the immune system, wherein the pharmaceutical composition is administered subcutaneously.

In a further aspect, the invention relates to a pharmaceutical composition suitable for subcutaneous administration comprising from 0.45 mg to 18.90 mg of a compound selected from the group consisting of:

(a) a C4BP isoform lacking the beta chain wherein if at least one of the alpha-chains forming said isoform is a deletion mutant which lacks at least one of the CCP domains, the CCP6 domain is preserved in said alpha-chain;

(b) a polypeptide comprising a full-length C4BP alpha-chain or a deletion mutant thereof that preserves the CCP6 domain; and (c) a polypeptide comprising the CCP6 domain of the C4BP alpha-chain or a functionally equivalent variant of said CCP6 domain and a pharmaceutically acceptable excipient suitable for subcutaneous administration, wherein if the compound is a C4BP isoform lacking the beta chain selected from the group consisting of $\alpha_7\beta_0$, $\alpha_6\beta_0$ and combinations thereof, the composition is not a composition of 0.5 mg of said isoform.

In a further aspect, the invention relates to a pharmaceutical composition suitable for subcutaneous administration comprising from 0.45 mg to 18.90 mg of a compound selected from the group consisting of:

(a) a C4BP isoform lacking the beta chain wherein if at least one of the alpha-chains forming said isoform is a deletion mutant which lacks at least one of the CCP domains, the CCP6 domain is preserved in said alpha-chain;

(b) a polypeptide comprising a full-length C4BP alpha-chain or a deletion mutant thereof that preserves the CCP6 domain; and (c) a polypeptide comprising the CCP6 domain of the C4BP alpha-chain or a functionally equivalent variant of said CCP6 domain and a pharmaceutically acceptable excipient suitable for subcutaneous administration, wherein if the compound is a C4BP isoform lacking the beta chain selected from the group consisting of $\alpha_7\beta_0$, $\alpha_6\beta_0$ and combinations thereof, the composition is not a composition of 4 mg of said isoform.

In a further aspect, the invention relates to a pharmaceutical composition suitable for subcutaneous administration comprising from 0.45 mg to 18.90 mg of a compound selected from the group consisting of:

(a) a C4BP isoform lacking the beta chain wherein if at least one of the alpha-chains forming said isoform is a deletion mutant which lacks at least one of the CCP domains, the CCP6 domain is preserved in said alpha-chain;

(b) a polypeptide comprising a full-length C4BP alpha-chain or a deletion mutant thereof that preserves the CCP6 domain; and (c) a polypeptide comprising the CCP6 domain of the C4BP alpha-chain or a functionally equivalent variant of said CCP6 domain and a pharmaceutically acceptable excipient suitable for subcutaneous administration, wherein if the compound is a C4BP isoform lacking the beta chain selected from the group consisting of $\alpha_7\beta_0$, $\alpha_6\beta_0$ and combinations thereof, the composition is a composition selected from the group consisting of:

(i) a composition comprising from 0.45 mg to 0.49 mg;

(ii) a composition comprising from 0.51 mg to 3.99 mg;

(iii) a composition comprising from 4.10 mg to 18.90 mg.

All the embodiments disclosed in the context of the first and second aspects of the invention are also applicable to these aspects.

The pharmaceutical composition comprises from 0.45 mg to 18.90 mg of a compound of the invention, more preferably from 0.45 mg to 9.45 mg, more preferably from 0.56 mg to 8.51 mg, more preferably from 0.75 mg to 8.13 mg, even more preferably from 0.79 mg to 8.05 mg. In a preferred embodiment, the dose is 0.79 mg. In another preferred embodiment, the dose is 0.8 mg. In another preferred embodiment, the dose is 8 mg. In another preferred embodiment, the dose is 8.05 mg.

In an embodiment, the pharmaceutical composition comprises from 7.56 mg to 18.90 mg of a compound of the invention, preferably from 9.45 mg to 15.13 mg, preferably from 11.35 mg to 15.13 mg, preferably from 13.24 mg to 15.13 mg.

In an embodiment, the pharmaceutical composition comprises from 1.89 mg to 17.02 mg of a compound of the invention, preferably from 3.78 mg to 15.13 mg, preferably from 5.67 mg to 13.24 mg, more preferably from 7.56 mg to 11.35 mg.

In an embodiment, the pharmaceutical composition comprises from 0.5 mg to 9 mg of a compound of the invention, more preferably from 0.75 mg to 8.5 mg. In another embodiment, the composition comprises from 7 mg to 18.90 mg of a compound of the invention, more preferably from 7.5 mg to 18 mg, more preferably from 9 mg to 15 mg, more preferably from 11 mg to 15 mg, even more preferably from 13 mg to 15 mg. In another embodiment, the pharmaceutical composition comprises from 1 mg to 17 mg of a compound of the invention, preferably from 3 mg to 15 mg, preferably from 5 mg to 13 mg, more preferably from 7 mg to 11 mg.

A composition may be a pharmaceutical composition that is a sterile aqueous or non-aqueous solution, suspension or emulsion, which additionally comprises a physiologically acceptable or suitable carrier. A pharmaceutically acceptable or suitable carrier may include (or refer to) an excipient (i.e., a non-toxic material that does not interfere with the activity of the active ingredient) and/or a diluent. Alternatively, compositions described herein may be formulated as a lyophilizate, or compounds may be encapsulated within liposomes using technology known in the art. Pharmaceutical compositions may also contain other components, which may be biologically active or inactive. Such components include, but are not limited to, buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, stabilizers, dyes, flavoring agents, and suspending agents and/or preservatives.

Any suitable excipient or carrier for subcutaneous administration known to those of ordinary skill in the art for use in pharmaceutical compositions may be employed in the compositions described herein. Excipients for therapeutic use are well known, and are described, for example, in Remingtons Pharmaceutical Sciences, Mack Publishing Co.

(A. R. Gennaro ed. 1985). For parenteral administration, the carrier preferably comprises water, saline, alcohol, a fat, a wax or a buffer. Excipients suitable for subcutaneous administration are, without limitation, alkylsaccharides, neutral polymers (polyvinylpyrrolidones, Ficoll-70000, hydroxyethyl (heta) starch, or PEG 4000), aluminum chloride, aluminium hydroxide, L-arginine, m-cresol, human serum albumin, hydrolyzed gelatin, D,L-methionine, monobasic sodium phosphate, polyoxyethylene sorbitan monolaurate, potassium pyrosulfite, sodium thioglycolate, α-thioglycerol and zinc chloride solution.

A pharmaceutical composition (for delivery by injection) may be in the form of a liquid. A liquid pharmaceutical composition may include, for example, one or more of the following: a sterile diluent such as water for injection, saline solution, preferably physiological saline, Ringer's solution, isotonic sodium chloride, fixed oils that may serve as the solvent or suspending medium, polyethylene glycols, glycerin, propylene glycol or other solvents; antibacterial agents; antioxidants; chelating agents; buffers and agents for the adjustment of tonicity such as sodium chloride or dextrose. A parenteral preparation can be enclosed in ampoules, disposable syringes or multiple dose vials made of glass or plastic. The use of physiological saline is preferred, and an injectable pharmaceutical composition is preferably sterile.

The agents described herein may be formulated for sustained or slow release. Such compositions may generally be prepared using well known technology and administered by subcutaneous implantation. Sustained-release formulations may contain an agent dispersed in a carrier matrix and/or contained within a reservoir surrounded by a rate controlling membrane. Excipients for use within such formulations are biocompatible, and may also be biodegradable; preferably the formulation provides a relatively constant level of active component release. The amount of active compound contained within a sustained release formulation depends upon the site of implantation, the rate and expected duration of release, and the nature of the condition to be treated or prevented.

Pharmaceutical compositions may be administered in a manner appropriate to the disease to be treated (or prevented) as determined by persons skilled in the medical art.

Patients may generally be monitored for therapeutic or prophylactic effectiveness using assays suitable for the condition being treated or prevented, which assays will be familiar to those having ordinary skill in the art. When administered in a liquid form, suitable dose sizes will vary with the size of the patient, but will typically range from about 1 ml to about 500 ml.

In a preferred embodiment, the pharmaceutical composition is administered in combination with one or more therapeutic agents useful in the treatment of an immunological disease caused by an undesired activation of the immune system.

In a preferred embodiment, the pharmaceutical composition is administered in a regimen comprising a plurality of administrations and wherein the pharmaceutical composition is administered no more than once a week.

Additional Aspects

In another aspect, the invention relates to a compound selected from the group consisting of:

a) a C4BP isoform lacking the beta chain wherein if at least one of the alpha-chains forming said isoform is a deletion mutant which lacks at least one of the CCP domains, the CCP6 domain is preserved in said alpha-chain;

b) a polypeptide comprising a full-length C4BP alpha-chain or a deletion mutant thereof that preserves the CCP6 domain; and c) a polypeptide comprising the CCP6 domain of the C4BP alpha-chain or a functionally equivalent variant of said CCP6 domain for use in the prevention and/or treatment of an immunological disease caused by an undesired activation of the immune system, wherein the compound is administered subcutaneously at a dose of from 0.24 μg/m$^2$ to 9.99 mg/m$^2$.

In an embodiment, the compound is administered at a dose of from 0.24 μg/m$^2$ to 0.24 mg/m$^2$, preferably from 1 μg/m$^2$ to 0.24 mg/m$^2$, preferably from 10 μg/m$^2$ to 0.24 mg/m$^2$, preferably from 50 μg/m$^2$ to 0.24 mg/m$^2$, more preferably from 100 μg/m$^2$ to 0.24 mg/m$^2$, more preferably from 150 μg/m$^2$ to 0.24 mg/m$^2$, more preferably from 200 μg/m$^2$ to 0.24 mg/m$^2$.

All the embodiments disclosed in the context of the previous aspects are applicable to this additional aspect.

In another aspect, the invention relates to a pharmaceutical composition comprising from 4.5 μg to 18.90 mg of a compound selected from the group consisting of:

(a) a C4BP isoform lacking the beta chain wherein if at least one of the alpha-chains forming said isoform is a deletion mutant which lacks at least one of the CCP domains, the CCP6 domain is preserved in said alpha-chain;

(b) a polypeptide comprising a full-length C4BP alpha-chain or a deletion mutant thereof that preserves the CCP6 domain; and (c) a polypeptide comprising the CCP6 domain of the C4BP alpha-chain or a functionally equivalent variant of said CCP6 domain and a pharmaceutically acceptable excipient suitable for subcutaneous administration for use in the prevention and/or treatment of an immunological disease caused by an undesired activation of the immune system, wherein the pharmaceutical composition is administered subcutaneously.

In a further aspect, the invention relates to a pharmaceutical composition suitable for subcutaneous administration comprising from 0.45 μg to 18.90 mg of a compound selected from the group consisting of:

(a) a C4BP isoform lacking the beta chain wherein if at least one of the alpha-chains forming said isoform is a deletion mutant which lacks at least one of the CCP domains, the CCP6 domain is preserved in said alpha-chain;

(b) a polypeptide comprising a full-length C4BP alpha-chain or a deletion mutant thereof that preserves the CCP6 domain; and (c) a polypeptide comprising the CCP6 domain of the C4BP alpha-chain or a functionally equivalent variant of said CCP6 domain and a pharmaceutically acceptable excipient suitable for subcutaneous administration, wherein if the compound is a C4BP isoform lacking the beta chain selected from the group consisting of $\alpha_7\beta_0$, $\alpha_6\beta_0$ and combinations thereof, the composition is a composition selected from the group consisting of:

(i) a composition comprising from 0.45 μg to 0.49 mg;

(ii) a composition comprising from 0.51 mg to 3.99 mg;

(iii) a composition comprising from 4.10 mg to 18.90 mg.

In an embodiment, the pharmaceutical composition comprises from 4.5 μg to 4.5 mg, preferably from 10 μg to 4.5 mg, more preferably from 25 μg to 4.5 mg, more preferably from 50 μg to 4.5 mg, more preferably from 100 μg to 4.5 mg, more preferably from 150 μg to 4.5 mg, more preferably from 200 μg to 4.5 mg, more preferably from 250 μg to 4.5 mg, preferably from 500 μg to 4.5 mg, preferably from 1000 μg to 4.5 mg, preferably from 1500 μg to 4.5 mg, preferably from 2000 μg to 4.5 mg, preferably from 2500 μg to 4.5 mg, preferably from 3000 μg to 4.5 mg, preferably from 3500 μg to 4.5 mg, more preferably from 4000 μg to 4.5 mg.

All the embodiments disclosed in the context of the previous aspects are applicable to said additional aspects.

The invention is also directed to:

1. A compound selected from the group consisting of:
   a) a C4BP isoform lacking the beta chain wherein if at least one of the alpha-chains forming said isoform is a deletion mutant which lacks at least one of the CCP domains, the CCP6 domain is preserved in said alpha-chain;
   b) a polypeptide comprising a full-length C4BP alpha-chain or a deletion mutant thereof that preserves the CCP6 domain; and
   c) a polypeptide comprising the CCP6 domain of the C4BP alpha-chain or a functionally equivalent variant of said CCP6 domain for use in the prevention and/or treatment of an immunological disease caused by an undesired activation of the immune system, wherein the compound is administered subcutaneously in a regimen comprising a plurality of administrations and wherein the compound is administered no more than once a week.
2. The compound for use according to [1], wherein the dose of each administration ranges from 0.24 $mg/m^2$ to 9.99 $mg/m^2$.
3. A compound selected from the group consisting of:
   a) a C4BP isoform lacking the beta chain wherein if at least one of the alpha-chains forming said isoform is a deletion mutant which lacks at least one of the CCP domains, the CCP6 domain is preserved in said alpha-chain;
   b) a polypeptide comprising a full-length C4BP alpha-chain or a deletion mutant thereof that preserves the CCP6 domain; and
   c) a polypeptide comprising the CCP6 domain of the C4BP alpha-chain or a functionally equivalent variant of said CCP6 domain for use in the prevention and/or treatment of an immunological disease caused by an undesired activation of the immune system, wherein the compound is administered subcutaneously at a dose of from 0.24 $mg/m^2$ to 9.99 $mg/m^2$.
4. The compound for use according to any one of [1] to [3], wherein the compound is administered once every two weeks.
5. The compound for use according to any one of [1] to [3], wherein the compound is administered once a week.
6. The compound for use according to any one of [1] to [5], further comprising a previous step of subcutaneous administration of the compound separated by less than seven days from the subsequent administration.
7. The compound for use according to [6], wherein the dose administered at the previous step and the dose administered in each subsequent administration is the same.
8. The compound for use according to [6], wherein the dose administered at the previous step is higher than the dose administered in each subsequent administration.
9. The compound for use according to any one of [1] to [8], wherein the immunological disease is an autoimmune disease.
10. The compound for use according to [9], wherein the autoimmune disease is selected from the group consisting of systemic lupus erythematosus, lupus nephritis, and rheumatoid arthritis.
11. The compound for use according to [10], wherein the autoimmune disease is rheumatoid arthritis.
12. The compound for use according to [10], wherein the autoimmune disease is selected from the group consisting of systemic lupus erythematosus and lupus nephritis.
13. The compound for use according to any one of [1] to [12], wherein the C4BP isoform lacking the beta chain is selected from the group consisting of $\alpha_7\beta_0$, $\alpha_6\beta_0$ and combinations thereof.
14. The compound for use according to any one of [1] to [12], wherein the deletion mutant lacks domains CCP1, CCP2, CCP3 and CCP4 of the C4BP alpha-chain.
15. The compound for use according to any one of [1] to [14], in which each Lys residue in the CCP8 domain of the C4BP alpha-chain has been replaced by a residue selected from the group consisting of Pro, Asp, Glu, His, Ile, Ala, Ser, Thr, Val, Gln and Asn.
16. The compound for use according to any one of [1] to [12], wherein the polypeptide comprising a functionally equivalent variant of the CCP6 domain of the C4BP alpha-chain is a polypeptide comprising SEQ ID NO: 2, SEQ ID NO: 3, SEQ ID N: 4 or SEQ ID NO: 5.
17. The compound for use according to any one of [1] to [16], wherein the compound is administered to a mammal.
18. The compound for use according to [17], wherein the mammal is a human.
19. The compound for use according to any one of [2] to [18], wherein the dose ranges from 4 $mg/m^2$ to 6 $mg/m^2$.
20. The compound for use according to any one of [1] to [19], wherein the compound is administered in combination with one or more therapeutic agents useful in the treatment of an immunological disease caused by an undesired activation of the immune system.
21. The compound for use according to [20], wherein the therapeutic agent useful in the treatment of an immunological disease caused by an undesired activation of the immune system is selected from the group consisting of infliximab, adalimumab, certolizumab, golimumab, etanercept, rituximab, epratuzumab, belimumab, rapamycin, anti-interferon antibodies, tocilizumab, laquinimod, tabalumab, ofatumumab, ixekizumab, brodalumab, briakinumab, sarilumab, rilonacept, anifrolumab, cyclophosphamide, mycophenolate mofetil, azathioprine, anticalcineurinics, prednisolone, methylprednisolone, vitamin D, vasoactive intestinal peptide, hydroxychloroquine, chloroquine, ocrelizumab, atacicept, abatacept, alemtuzumab, sirukumab, eculizumab and T cell vaccine.
22. Pharmaceutical composition comprising from 0.45 mg to 18.90 mg of a compound selected from the group consisting of:
   (a) a C4BP isoform lacking the beta chain wherein if at least one of the alpha-chains forming said isoform is a deletion mutant which lacks at least one of the CCP domains, the CCP6 domain is preserved in said alpha-chain;
   (b) a polypeptide comprising a full-length C4BP alpha-chain or a deletion mutant thereof that preserves the CCP6 domain; and (c) a polypeptide comprising the CCP6 domain of the C4BP alpha-chain or a functionally equivalent variant of said CCP6 domain and a pharmaceutically acceptable excipient suitable for subcutaneous administration for use in the prevention and/or treatment of an immunological disease caused by an undesired activation of the immune system, wherein the pharmaceutical composition is administered subcutaneously.

23. Pharmaceutical composition for use according to [22], wherein the pharmaceutical composition is administered in a regimen comprising a plurality of administrations and wherein the pharmaceutical composition is administered no more than once a week.

The invention is described in detail by way of the following examples which are to be considered as merely illustrative and not limitative of the scope of the invention.

EXAMPLES

Example 1: Engineering Novel C4BP(β−)-Based Immunomodulatory Molecules

In order to: 1) differentiate the relative contribution of C4BP(β−) to complement inhibition and to immunomodulation in inflammatory DCs using in vivo animal models of autoimmunity; and 2) discard the contribution of certain C4BP(β−) pathogen- and plasminogen-binding domains to general immunosuppression, the inventors have genetically engineered mutants of the C4BP α-chain:

Mutant 1: CCP1-CCP4 α-chain deletion mutant: the structure of the mutant is C4BP(CCP5-CCP8)($\alpha_7\beta_0$). This mutant lacks the complement inhibitory activity (retained in domains CCP1-CCP3), and also does not bind to a variety of pathogens that bind C4BP through this region. However, it retains the immunomodulatory activity over DCs, ascribed to CCP6.

Mutant 2: Combined CCP1-CCP4 deletion and $CCP8_{lys}$ α-chain mutant: This mutant lacks the complement inhibitory activity (retained in domains CCP1-CCP3), therefore does not bind to a variety of pathogens that bind C4BP through this region. Moreover, the inventors replaced the 3 positively charged Lys residues in the C4BP CCP8 α-chain by Gin residues, to reduce plasminogen binding without compromising the immunomodulatory activity of C4BP(β−).

Methods

Mutants

Mutants 1 and 2 DNAs were cloned into pCDNA3.1(+) expression vector. Plasmid DNAs were amplified and purified using a Qiafilter Plasmid MegaKit, Qiagen.

Proteins

Recombinant C4BP(β−) (rC4BP(β−) and mutants 1 and 2 were transiently produced in HEK293 cells (Expi293 cells). rC4BP(β−) was purified from the cell culture supernatants following "Bioingenium" protocols which comprise a centrifugation step and three chromatographic steps wherein the sample was subsequently submitted to addition of NaCl, a hydrophobic interaction chromatography column (HiScreen Butyl FF column), concentration and diafiltration, an anion exchange chromatography column (HiScreen Q HP column), concentration and a size exclusion chromatography column (HiLoad 16/60 superdex 200 μg column). The sample was finally subjected to concentration and dialysis steps. The mutants were purified from the cell culture supernatants by a butyl chromatography followed by concentration and diafiltration. After that, the sample mutants were submitted to Q anion exchange chromatography and then dialyzed.

Polyacrylamide Gel Electrophoresis

In order to analyze whether C4BP(β−) mutants form oligomeric structures, Coomassie stained 12% SDS-PAGE were performed in reducing and non-reducing conditions.

In Vitro Functional Assessment of the Immunomodulatory Activity of Full-Length C4BP(β−) and C4BP(β−) Variants Over DCs The inventors used for the in vitro study both C4BP(β+) (WT) and recombinant C4BP(β−) isoforms, and the above-referred mutants or variants: Mutant 1 and Mutant 2. C4BP (β+) isoforms refer to the major C4BP $\alpha_7\beta_1$ plus the minor C4BP $\alpha_6\beta_1$ isoforms (both in complex with ProS) purified from pooled human plasma. C4BP(β+) has no immunomodulatory activity and has been used as a negative control in the assays (Olivar et al. 2013. J. Immunol. 190:2857-72).

RPMI 1640 was supplemented with 100 μg/ml of streptomycin, 100 IU/ml of penicillin, 2 mM L-glutamine (all from Invitrogen, Carlsbad, CA) and 10% heat-inactivated fetal bovine serum (Linus, Cultek, Spain) (complete medium), unless otherwise stated.

Peripheral blood mononuclear cells (PBMCs) were obtained from buffy coat preparations collected from healthy donors from the Blood and Tissue Bank (Barcelona, Spain) after Ficoll-Paque™ density centrifugation (GE Healthcare Bio-Sciences AB; Uppsala, Sweden). For surface phenotype determination, monocytes were plated at $1\times10^6$ cells/ml in 60 mm culture plates (Corning, Spain), in RPMI 1640 medium without serum, and allowed to adhere for 2 h at 37° C. in 5% $CO_2$. The non-adherent cells were removed by washing in PBS. The final population contains >75% of monocytes, as demonstrated by flow cytometry of anti-CD14-stained isolates.

Monocyte-derived DCs were generated supplementing the monocyte cultures with complete RPMI 1640 medium plus GM-CSF (800 UI/ml) and IL-4 (500 UI/ml) (both from Gentaur, Kampenhout, Belgium) at day 0 and day 3 of culture. For DC maturation, at day 5 iDCs were further stimulated for 48 h with 5 μg/ml LPS (*Escherichia coli* 055.B5, Sigma L2880, Copenhagen, Denmark).

Staining using the fluorescent dye 7-amino-actinomycin D (7-AAD) (BD Pharmigen) and flow cytometry analysis was employed to assess the viability status of C4BP-treated and untreated DCs.

Cell surface phenotypes were analyzed by flow cytometry using the following mAbs: FITC-conjugated anti-CD83 (HB15a) and PE-conjugated anti-CD86 (HA5.2B7) (all from Beckman-Coulter). The respective isotype controls FITC-conjugated anti-IgG2b (H2) and PE-conjugated anti-IgG2b (H2), were from the same commercial sources. After washing with PBS, cells were subsequently stained with 3 μl mAb/$10^5$ cells in 100 μl of FACS buffer (PBS containing 1% BSA and 0.1% sodium azide) for 20 min at room temperature. To exclude dead cells and debris, DCs were gated according to forward scatter (FSC) and side scatter (SSC) parameters. Stained cells were analyzed using a FACSCalibur (Becton Dickinson, Franklin Lakes, NJ) equipped with CellQuestPro software (Becton Dickinson).

ELISA Assays

Secretion of IL-12p70 from both untreated or treated DCs with the C4BP isoforms and variants under study was assessed with a "DuoSet ELISA Kit" (R&D Systems, Minneapolis, MN) according to the manufacturer's instructions.

Results

Figure 1:
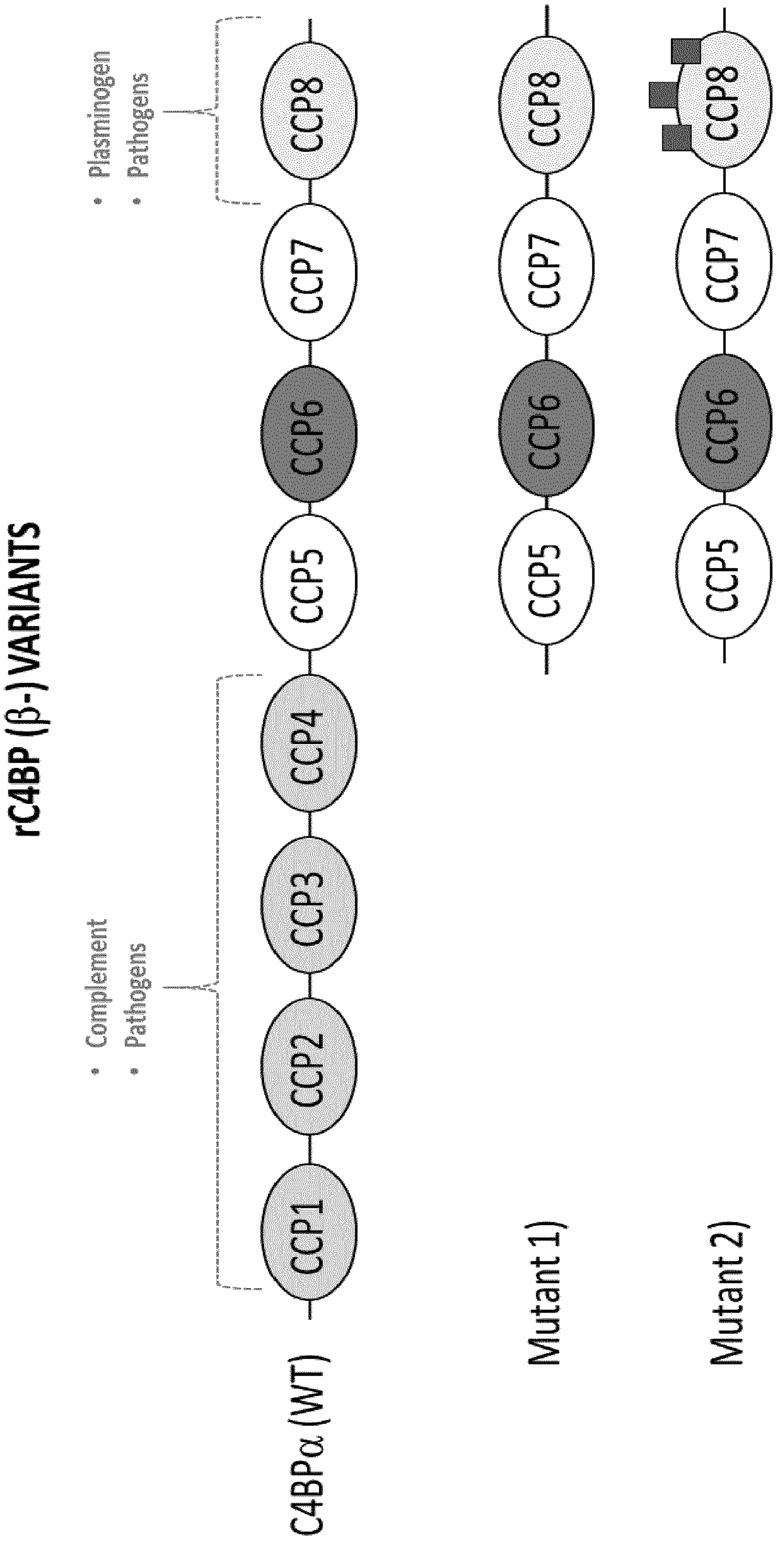
FIG. 1. Schematic representation of the C4BPα chain and the engineered variants. The wild type C4BPα chain is build up of eight CCP domains arranged linearly. The N-terminal domains (CCP1-CCP4) bind complement C4b and a variety of pathogens and host proteins. The C-terminal CCP8 domain is involved in plasminogen and pathogen binding. The internal CCP6 domain possesses immunomodulatory activity. Deletion mutant 1 lacks the N-terminal domains (CCP1-CCP4) and therefore is unable to modulate the complement system and to bind to a variety of pathogens. Deletion mutant 2 is analogous to deletion mutant 1 but additionally the 3 positively charged Lys residues in the CCP8 domain have been replaced by Gln residues to avoid plasminogen binding.

To dissect the different C4BP(β−) activities, the inventors genetically engineered the C4BP β-chain to obtain protein mutants: i) Mutant 1, lacking domains CCP1-CCP4 (to avoid complement inhibition and pathogen binding), and ii) Mutant 2, combining CCP1-CCP4 deletion and $CCP8_{Lys \rightarrow Gln}$ mutations (to avoid complement inhibition, pathogen binding and plasminogen binding) (FIG. 1). All variants should preserve the immunomodulatory activity, which has been mapped to the CCP6 domain of C4BP(β−).

Figure 2:
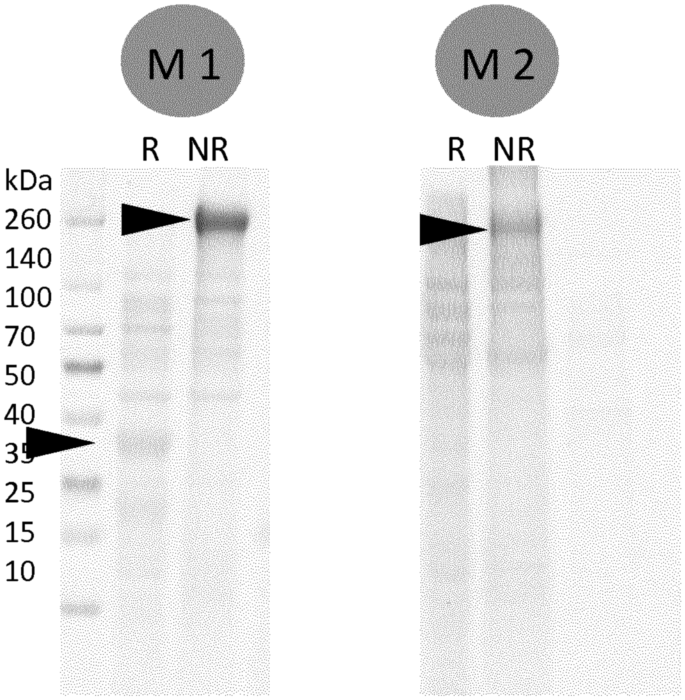
FIG. 2. Electrophoretic analysis of rC4BP(β−) mutant production and oligomerization. The configuration of the C4BP(β−) mutants 1 and 2 (M1, M2) was assessed by 12% SDS-PAGE both under reducing (R) and non-reducing (NR) conditions. Each lane was loaded with 10 μg purified protein and stained with Coomasie Blue. Left lane, molecular weight standard.

The purified proteins were first detected by SDS-PAGE under both reducing and non-reducing conditions. Higher molecular weight bands were seen in non-reducing conditions compared to reduced conditions, which confirmed the correct size and oligomerization status (~240 kDa) of the engineered mutants (FIG. 2).

The inventors then aimed to further characterize the structural mutants of the C4BP(β−) isoform for its immunomodulatory or "tolerogenic" activity over DCs. Thus, recombinant C4BP (α6β0) mutants lacking different CCP domains but preserving in all cases the CCP6 domain (FIG. 1) were tested for their ability to affect the activation phenotype of DCs. All individual deletion mutants were able not only to significantly prevent the up-regulation of the CD83 and CD86 DC surface maturation markers (FIGS. 3A and 3B), but also to preclude IL-12p70 production, a central DC pro-inflammatory cytokine mediating Th1 polarization (FIG. 3C).

Example 2: Dose-Response Study. Therapeutic Efficacy of C4BP(β−) to Prevent and/or Attenuate Systemic Lupus Erythematosus (SLE) in a Mouse Model This study evaluated the efficacy of recombinant C4BP (β−) (that has been shown to act over dendritic cells (DCs) through induction of a tolerogenic, anti-inflammatory phenotype) in the attenuation of lupus nephritis progression occurring in the spontaneous SLE mouse model NZBWF1 (NZB/NZW F1). Other variables that were investigated were the route of administration and dose.

Materials and Methods

Proteins and Drugs

Recombinant C4BP(β−) (rC4BP(β−)) (batch #Jan12008-P03) was transiently produced in HEK293 cells (Expi293 cells) and purified from the cell culture supernatants according to the protocol followed for Example 1. rC4BP(β−) was supplied in PBS buffer, pH 7.4 at a concentration of 5.6 mg/ml (7 aliquots of 1.0 ml and 1 aliquot of 0.2 ml; 40.32 mg total protein). The inventors used a second batch of purified rC4BP(β−) (batch #Jan12008-P04) at a concentration of 4.8 mg/ml (4 aliquots of 1.0 ml and 1 aliquot of 0.05 ml; 19.3 mg total protein). The purity of both protein batches was ~80%, as assessed by SDS-electrophoresis.

Cyclophosphamide (Genoxal®, Baxter, batch #88057) was diluted in saline and administered at a dose of 2.5 mg in a final volume of 0.13 ml.

In Vitro Functional Assessment of C4BP(β−) Immunomodulatory Activity Over DCs

The inventors used for the in vitro study both C4BP(+) and C4BP(β−) isoforms. C4BP(3+) isoforms refer to the major C4BP $\alpha_7\beta_1$ plus the minor C4BP $\alpha_6\beta_1$ isoforms (both in complex with ProS) purified from pooled human plasma, as previously described (Dahlbäck B. 1983. Biochem J., 209:847-56). C4BP(3+) has no immunomodulatory activity and has been used as a negative control in the assays (Olivar et al. 2013. J. Immunol., 190:2857-72).

RPMI 1640 was supplemented with 100 μg/ml of streptomycin, 100 IU/ml of penicillin, 2 mM L-glutamine (all from Invitrogen, Carlsbad, CA) and 10% heat-inactivated fetal bovine serum (Linus, Cultek, Spain) (complete medium), unless otherwise stated.

Peripheral blood mononuclear cells (PBMCs) were obtained from buffy coat preparations collected from healthy donors from the Blood and Tissue Bank (Barcelona, Spain) after Ficoll-Paque™ density centrifugation (GE Healthcare Bio-Sciences AB; Uppsala, Sweden). For surface phenotype determination, monocytes were plated at $1 \times 10^6$ cells/ml in 60 mm culture plates (Corning, Spain), in RPMI 1640 medium without serum, and allowed to adhere for 2 h at 37° C. in 5% $CO_2$. The non-adherent cells were removed by washing in PBS. The final population contained >75% of monocytes, as demonstrated by flow cytometry of anti-CD14-stained isolates.

Monocyte-derived DCs were generated supplementing the monocyte cultures with complete RPMI 1640 medium plus GM-CSF (800 UI/ml) and IL-4 (500 UI/ml) (both from Gentaur, Kampenhout, Belgium) at day 0 and day 3 of culture. For DC maturation, at day 5 iDCs were further stimulated for 48 h with 5 μg/ml LPS (*Escherichia coli* 055.B5, Sigma L2880, Copenhagen, Denmark).

Staining using the fluorescent dye 7-amino-actinomycin D (7-AAD) (BD Pharmigen) and flow cytometry analysis was employed to assess the viability status of C4BP-treated and untreated DCs.

Cell surface phenotypes were analyzed by flow cytometry using the following mAbs: FITC-conjugated anti-CD83 (HB15a) and PE-conjugated anti-CD86 (HA5.2B7) (all from Beckman-Coulter). The respective isotype controls FITC-conjugated anti-IgG2b (H2) and PE-conjugated anti-IgG2b (H2), were from the same commercial sources. After washing with PBS, cells were subsequently stained with 3 μl mAb/$10^5$ cells in 100 μl of FACS buffer (PBS containing 1% BSA and 0.1% sodium azide) for 20 min at room temperature. To exclude dead cells and debris, DCs were gated according to forward scatter (FSC) and side scatter (SSC) parameters. Stained cells were analyzed using a FACSCalibur (Becton Dickinson, Franklin Lakes, NJ) equipped with CellQuestPro software (Becton Dickinson).

Mice, Study Design and Follow Up

NZB/NZW F1 or NZBWF1/J (Charles-River), NZB/NZW F1 (Jackson, code 100008) are a hybrid cross between NZB/B1NJ (Jackson, code 000684) Female x NZW/LacJ (Jackson, code 001058) Male. NZBWF1/J mice develop an autoimmune disease resembling human systemic lupus erythematosus. The inventors used 58 females (30-35 g/each) aged 15 weeks for the study (4-5 animals per cage). The animals were maintained under standard laboratory conditions, at 20-24° C. and 40-70% relative humidity, with 12-hour fluorescent light/12-hour dark cycle. They were feed standard diet and tap water ad libitum.

The NZBWF1 model of spontaneous SLE is the oldest and most commonly used of the classical models of SLE (Rottman and Willis. 2010. Vet. Pathol., 47:664-76). A cross between New Zealand Black and New Zealand White (NZB/W) mice, the F1 hybrid strain, develops severe lupus-like phenotypes that resemble human SLE (Perry et al. 2011. J. Biomed. Biotechnol., 2011:271694). As in humans, multiple genes contribute to the pathogenesis of SLE. In NZBWF1 mice, these genes include major histocompatibility complex (MHC) as well as several non-MHC genes. Similar to human SLE, the disease in NZBWF1 mice has a strong bias in favor of females, which also suggests a pathogenic role of estrogen. Clinical manifestations of SLE in this model include hyperactive B and T cells, high titers of several autoantibodies directed against nuclear antigens, defective clearance of immune complexes, and fatal immune glomerulonephritis. Because the model has been in use since the early 1960s, it is well characterized with much comparative data available.

Dose Selection and Administration.

The selection of the C4BP(β−) dose for in vivo administration was based in previous studies employing complement-related proteins in immune-inflammatory pathologies. Blom et al. (Blom et al. 2009. Ann. Rheum. Dis., 68:136-42) used the C4BP isoform lacking β chain in experimental collagen-induced arthritis (CIA) and collagen antibody-induced arthritis (CAIA) mice to investigate the influence of complement activity in the treatment of rheumatoid arthritis. These authors administered intraperitoneally C4BP (2 mg/mouse) using a multiple dose-regimen once every two days in preventive and therapeutic experiments. Thus, in the current study, C4BP(β−) was administered both intraperitoneally (IP) and subcutaneously (SC) into NZBWF1 mice for three months (between six and nine months of age).

Cyclophosphamide has been described as treatment in SLE. Alperovich et al (Alperovich et al. 2007. Lupus, 16:18-24) administered cyclophosphamide (CYP) to NZBWF1 mice at 50 mg/kg IP every 10 days. These authors showed that serum anti-DNA antibodies were appropriately controlled in the CYP group, and CYP arrested and reversed almost all histological lesions.

Both IP and SC administrations for C4BP(β−), CYP and PBS (150 μl/each) were performed with a 25-gauge needle during 30 s, after rinsing the skin with 70% ethanol.

The detailed administration schedule was as follows (Table 5):

The sample collection schedule was as shown (Table 6):

TABLE 6

| Sample collection schedule after treatment in a mouse model of spontaneous SLE. | | | |
|---|---|---|---|
| | Weight | Urine | Blood |
| W20 | | | |
| W21 | X | X | X |
| W22 | | | |
| W23 | X | | |
| W24 | | Inoculation | |
| W25 | X | X | X |
| W26 | | Inoculation | |
| W27 | X | X | |
| W28 | | Inoculation | |
| W29 | X | X | X |
| W30 | | Inoculation | |
| W31 | X | | |
| W32 | | Inoculation | |
| W33 | X | X | X |
| W34 | | Inoculation | |
| W35 | X | | |
| W36 | | Inoculation | |
| W37 | X | X | X |
| W38 | X | | |
| W39 | X | | |
| W40 | X | | |

The animals were observed daily throughout the experimental period to check out any local and systemic reaction to the treatment, as well as other signs of illness and/or behavioral changes in order to obtain tolerance and toxicological information. Body weight was determined twice monthly from the beginning to the end of follow-up. Mice

TABLE 5

| Administration schedule of treatment in a mouse model of spontaneous SLE. | | | | | | | | | | | | | | | | |
|---|---|---|---|---|---|---|---|---|---|---|---|---|---|---|---|---|
| | | | | Treatment (μg protein/mouse) | | | | | | | | | | | | |
| Group | Treatment | Route | N | W24 | W25 | W26 | W27 | W28 | W29 | W30 | W31 | W32 | W33 | W34 | W35 | W36 |
| A | CYP | IP | 8 | | | | | | | | | | | | | |
| B | rC4BP | IP | 6 | 500 | | 500 | | 500 | | 500 | | 500 | | 500 | | 500 |
| C | rC4BP | IP | 6 | 50 | | 50 | | 50 | | 50 | | 50 | | 50 | | 50 |
| D | rC4BP | IP | 6 | 5 | | 5 | | 5 | | 5 | | 5 | | 5 | | 5 |
| F | rC4BP | SC | 6 | 50 | | 50 | | 50 | | 50 | | 50 | | 50 | | 50 |
| G | rC4BP | SC | 6 | 5 | | 5 | | 5 | | 5 | | 5 | | 5 | | 5 |
| H | rC4BP | SC | 6 | 500 | | | | 500 | | | | 500 | | | | 500 |
| I | PBS | IP | 8 | 0 | | 0 | | 0 | | 0 | | 0 | | 0 | | 0 |

N: number of mice; W: week; PBS: phosphate buffered saline, every 2 weeks up to week 36; CYP: Cyclophosphamide, IP (50 mg/kg), once every 10 days up to week 36; rC4BP: recombinant C4BP(β-) (W24-W26-W28-W30): administration of batch #Jan12008-P03 and rC4BP(β-) (W32-W34): administration of batch #Jan12008-P04 and rC4BP(β-); (W36): mixed administration of batch #Jan12008-P03 rC4BP(β-) and batch #150206 plasma-purified C4BP(β-).
IP: intraperitoneal administration. SC: subcutaneous administration Given the outcome of the proteinuria results at week 33, the inventors decided to perform one additional administration at week 36. Because of technical difficulties in the rC4BP(β−) purification, the recombinant protein available was not enough to complete this additional administration of all mouse groups at week 36. Thus, given the analogous functional performance of rC4BP(β−) and plasma-purified C4BP(β−) in the in vitro functional assays (see FIG. 4), the inventors determined to mix both proteins.

Consequently, the animals received, at week 36, a mixture of: 1,200 μl of plasma-purified C4BP(β−) (stock: 5.2 mg/ml; batch #150206)+484.8 μl rC4BP(β−) (stock: 5.6 mg/ml; batch #Jan12008-P03), being the final concentration of the protein mixture: 5.3 mg/ml.

were placed in metabolic cages to collect 24 h urine specimens before the onset of treatment and monthly thereafter. Blood was obtained from the tail vein at monthly intervals.

For the survival analysis, standard endpoint criteria were adopted for both the control (PBS) and C4BP(β−)- or CYP-treated mice (20% weight loss, and/or animal's condition: physical appearance, measurable clinical signs, unprovoked behavior and response to external stimuli) prior to euthanasia (NRC (National Research Council). 2010. Guide for the Care and Use of Laboratory Animals. Washington D.C.: National Academy of Sciences).

The experiments were carried out in accordance with current EU legislation on animal experimentation and were approved by "CEEA: Animal Experimentation Ethic Committee", the Institutional Ethics UB Committee for Animal Research. The corresponding animal experimentation procedure was approved by the Generalitat de Catalunya (DARP: 8765).

Renal Function Analysis: Proteinuria 24 h urinary protein was determined by pyrogallol red (Olympum Autoanalyzer AU400, Hamburg, Germany) in the Veterinary Clinical Biochemistry Laboratory from Universitat Autonoma de Barcelona.

Statistical Analysis

One-way analysis of variance (ANOVA) with post hoc tests was performed to compare proteinuria throughout the follow up. Survival data were analyzed using Kaplan-Meier curves and long-rank test. P value<0.05 was considered significant. Data are expressed as mean±SEM.

Results

Immunomodulatory Activity of rC4BP(β−) on MoDCs

Figure 4:
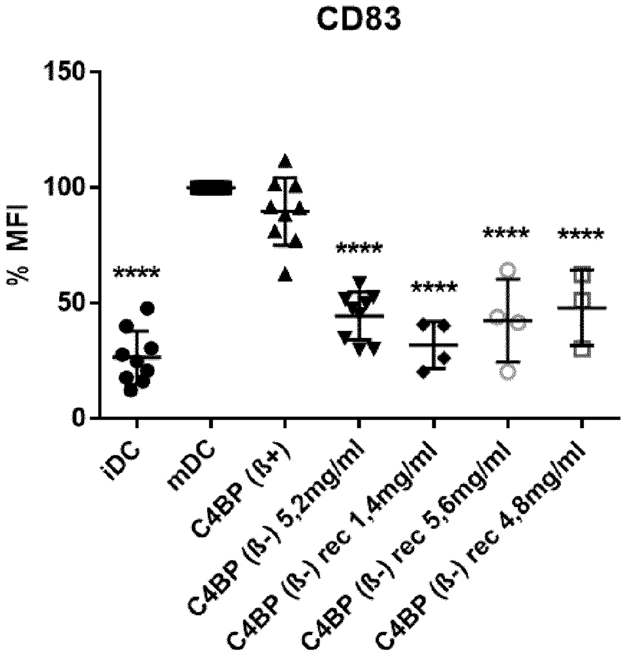
FIG. 4. Both plasma-purified and recombinant C4BP(β−) isoforms restrain similarly CD83 and CD86 surface marker expression in human MoDCs stimulated with LPS. Human MoDCs were incubated throughout their differentiation and maturation process with 5 μg/ml of the appropriate C4BP isoform. DC maturation was achieved by LPS treatment (5 μg/ml). Cells were collected, washed, and analyzed by flow cytometry for CD83 and CD86 (cluster of differentiation 83 and cluster of differentiation 86) cell-surface markers expression with specific fluorescence-labeled antibodies. iDC, untreated, immature DCs; mDC, untreated, LPS-matured DCs; C4BP(β+), C4BP major isoform-treated, LPS-matured DCs; C4BP(β−) 5.2 mg/ml, plasma-purified C4BP minor isoform (from Bioingenium's stock (5.2 mg/ml) (batch #141127))-treated, LPS-matured DCs; C4BP(β−) rec 1.4 mg/ml, recombinant C4BP minor isoform (from Bioingenium's initial semi-purified stock (1.4 mg/ml) (batch #0156160427))-treated, LPS-matured DCs; C4BP(β−) rec 5.6 mg/ml, recombinant C4BP minor isoform (from Bioingenium's first stock used in the present study (batch #Jan12008-P03; 5.6 mg/ml))-treated, LPS-matured DCs; C4BP(β−) rec 4.8 mg/ml, recombinant C4BP minor isoform (from Bioingenium's second stock used in the present study (batch #Jan12008-P04; 4.8 mg/ml))-treated, LPS-matured DCs. Results shown are the relative median fluorescence intensity (MFI)±SD from 3 to 9 independent PBMC donors. ****$p<0.0001$, compared with mDC.
Figure 4:
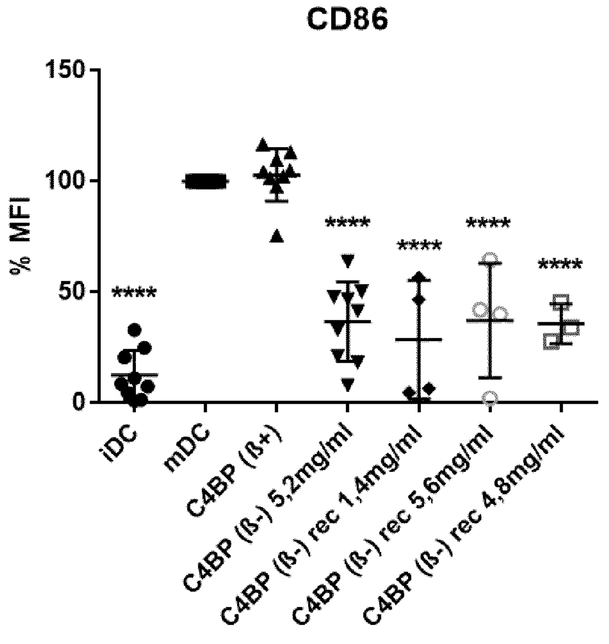

To assess the immunomodulatory activity of the rC4BP (β−) to be employed in the dose-response in vivo study, the inventors pre-incubated MoDCs with 5 μg/ml of purified rC4BP(β−) from different batches, and compared their performance to the active plasma-purified C4BP(β−) isoform tested in previous assays, or to the inactive C4BP(β+) isoform, after challenging these cells with the pro-inflammatory and maturation stimulus LPS. As previously published (Olivar et al. 2013. J. Immunol., 190:2857-72), both plasma-purified and rC4BP(β−), but not C4BP(β+), were able to confer an analogous semi-mature, anti-inflammatory phenotype to LPS-matured MoDCs, confirming the immunomodulatory activity of Bioingenium's-purified C4BP(β−) proteins (FIG. 4).

rC4BP(β−) Affects Renal Function and Survival in Lupus-Prone NZBWF1 Mice: Influence of the Route of Administration and Dose-Response Study Proteinuria is the most prominent and life-threatening symptom in lupus mice. It reflects the damage to the kidneys and closely correlates with disease outcome. Thus, in the present study the inventors inquired whether: 1) the route of rC4BP(β−) administration (intraperitoneal or subcutaneous), and/or 2) reducing rC4BP(β−) dosage and schedule of administration, were positively or negatively affecting renal function and survival outcome in rC4BP(β−)-treated NZBWF1 mice compared to PBS-treated control NZBWF1 mice.

Regarding the intraperitoneal (IP) administration route, proteinuria from PBS-treated control mice started to develop at week 27 and progressed steadily to severe proteinuria (>300 mg/kg) by week 31 (near 8 months of age) up to the end of the study (week 37) (FIG. 5A). In comparison, rC4BP(β−) treatments delayed the onset of proteinuria proportionally to the dose administered. Hence, administration once every two weeks of either 50 μg rC4BP(β−)/mouse or 5 μg rC4BP(β−)/mouse produced a 2-week delay in the onset of proteinuria, although by week 37 both mouse groups reached severe proteinuria indistinguishable from the PBS-treated control group (FIG. 5A). Interestingly, administration once every two weeks of 500 μg rC4BP(β−)/mouse was able to delay 6 weeks the onset of proteinuria respect to the PBS-treated control mice. Thus, by week 33 the corresponding mean proteinuria values from both groups were significantly different (p<0.05). Nevertheless, mice receiving 500 μg inoculations started to steadily increase the proteinuria level from week 33, nearly reaching the critical 300 mg protein/kg in the urine at the end of the study (week 37). This outcome was comparable to that achieved in a previous study employing 500 μg plasma-purified C4BP (β−)/mouse administered twice/week. Standard CYP administration (50 mg/kg every 10 days) prevented the development of proteinuria up to the end of the study (week 37) (FIG. 5A).

Concerning the subcutaneous administration route (SC), in mice treated SC with lower rC4BP(β−) doses (particularly, 50 μg rC4BP(β−) once every two weeks), the onset of proteinuria was significantly delayed ((p<0.05 at week 33), although a slight increase in proteinuria (<200 mg/kg) was observed by week 37 (end of the study) (FIG. 5B).

To note, neither toxicity nor behavioral changes were observed in the mice as a consequence of C4BP(β−) or CYP administration.

Kaplan-Meier curves were also plotted for each treatment group to investigate survival differences among groups. Thus, the control PBS-treated NZBWF1 mice all died during the period of observation and 50% of them were death at 300 days. In contrast, all mice receiving the standardized immunosuppressive CYP treatment survived throughout the period of observation, while the rC4BP(β−)-treated groups had variable outcomes. Regarding the IP route, the group administered with the lower rC4BP(β−) dose (5 μg) performed similarly to the control PBS-treated group, having all mice died at the end of the study (330 days). In contrast, mice receiving higher rC4BP(β−) doses (50 and 500 μg) prolonged their survival, and near 20-30%, were still alive at the end of the study (FIG. 6A). Concerning the SC route, only mice treated with 50 μg rC4BP(β−) seemed to appreciably delay their survival respect to the control PBS-treated mice. Nevertheless, all rC4BP(β−) treatment groups maintained mice active at the end of the study. Interestingly, in the 50 μg rC4BP(β−)-treated group more than 60% of mice were alive at 330 days. Nevertheless, because of the reduced size of the groups (n=6), statistical analysis of Kaplan-Meier survival curves from NZBWF1 mice showed no statistically significant differences between any of the rC4BP(β−)-treated groups and the control PBS-treated group (FIG. 6B).

Therefore, and in agreement with the proteinuria results, a substantial slowing of the progress of the disease was apparent in NZBWF1 mice treated SC with 50 μg rC4BP (β−).

Example 3: Evaluation of the Efficacy of C4BP Isoform Lacking Beta Chain in the CAIA Model in Mice Collagen-antibody induced arthritis (CAIA) is a simple mouse model of human rheumatoid arthritis (RA) induced by the systemic administration of a cocktail of monoclonal antibodies directed against conserved auto-antigenic collagen type II epitopes, followed by a single injection of lipopolysaccharide (LPS). CAIA is a useful model to study the effector inflammatory phase of arthritis without involving the priming phase of the immune response. The murine CAIA model shares several clinical, immunological and pathological features with RA. Therefore, this model is useful to study the pathogenic mechanisms involved in RA disease as well as for testing new therapies.

The aim of this study was to evaluate the efficacy of C4BP(β−) administered subcutaneously at different times in the CAIA model in mice.

Materials and Methods

Test System and Housing Conditions

Balb/c male mice aged 7-8 weeks were supplied by Envigo. The animals were acclimated during 12 days. The animals were maintained in an environmentally controlled room with ventilation, temperature (22±2° C.), relative humidity (35-65%), and cycle light/dark (12 h/12 h). The animals were housed in groups of 3-5 animals/cage. The maintenance diet was supplied by Harlan Interfauna Ibérica, S. L. ("2014 Harlan Teklad Global Diets") and they were feed diet and water ad libitum.

Test Items and Formulation

Plasmatic C4BP(β−) was supplied at a concentration of 6.2 mg/ml. C4BP(β−) solutions were prepared to the desired concentration 0.33 mg/ml (for 50 μg doses) by dilution with Dulbecco's phosphate-buffered saline (DPBS) of C4BP(β−) 6.2 mg/ml stock solution.

Two reference compounds were used: dexamethasone (Sigma, Ref. D1756) and Enbrel® (etanercept) (Pfizer, Ref. 655950).

Reference compound dexamethasone was dissolved in vehicle (0.1% Tween-80+99% carboxymethyl cellulose (CMC) (0.5% w/v) in water at a concentration of 0.1 mg/ml.

Enbrel® was prepared at 6 mg/ml in DPBS by dilution of 50 mg/mL stock solution.

Solutions were prepared immediately before their administration to the animals (see Table 7).

TABLE 7

Preparation of reference compound dexamethasone.

| DEXAMETHASONE | | | |
|---|---|---|---|
| Dose (mg/kg) | Volume (mL/kg) | Concentration (mg/mL) | Preparation (d4/5-11) |
| 1 | 10 | 0.1 | 1.5 mg + 15 mL vehicle |

Experimental Procedure

Day 0: Arthritis Induction

On day 0, animals for experimental group C4BPd3 were randomly selected (n=8) and identified using tail code numbers and weighted.

Each mouse was sensitized by the administration of 2 mg anti-type II collagen antibodies cocktail (ArthritoMAB™ cocktail solution, 0.2 mL, i.v., day 0) in the caudal vein.

Day 3: LPS Synchronization

Animals were intraperitoneally administered with 0.1 mL of LPS solution (0.7 mg/ml, 70 μg/animal).

Day 3: Treatment

50 μg of C4BP(β−) were administered subcutaneously at day 3 to treatment group C4BPd3.

Day 5: Treatment

50 μg of C4BP(β−) were administered subcutaneously at day 5 to treatment group C4BPd3.

Day 5: Animal Distribution

On day 5 after sensitization, the rest of the animals developing clinical signs of arthritis (n=18) were evaluated and distributed in base of CAIA+incidence. Animals were homogeneously randomized (arthritis score) into the CAIA control group, dexamethasone (1 mg/kg at days 5-11, p.o.) and Enbrel®-treated groups (30 mg/kg at days 5-11, s.c.) (n=6). Animals were identified using tail code numbers and weighted.

Group 2 was not included in the distribution because of the previous test item administration. Experimental groups are shown in Table 8.

TABLE 8

Experimental groups.

| Experimental group | Group identification | Sensitization ArthritoMAB ™ cocktail (d0) | Induction LPS, (d3) | Treatment | Day | Route | N |
|---|---|---|---|---|---|---|---|
| 1 | CAIA control | 0.2 mL iv | 0.1 mL ip | DPBS | 5-11 | sc | 6 |
| 2 | C4BPd3 | 0.2 mL iv | 0.1 mL ip | C4BP 50 μg | 3 and 5 | sc | 8 |
| 3 | Dexamethasone | 0.2 mL iv | 0.1 mL ip | dexamethasone 1 mg/kg | 5-11 | po | 6 |
| 4 | Enbrel ® | 0.2 mL iv | 0.1 mL ip | Enbrel ® 30 mg/kg | 5-11 | sc | 6 |

Arthritis Evaluation:

The arthritis score was determined using the criteria of Table 9.

TABLE 9

Evaluation of arthritis score.

| | |
|---|---|
| Front paws (score: 0-12) | Fingers: each arthritic (red and swollen) finger = 1 point<br>Final score = arthritic fingers / 2 (0-4)<br>Wrists: 1: slight redness, 2: moderate swelling, 3: severe swelling; 4: maximal inflammation (final score: 0-8) |
| Hind paws (score: 0-13) | Toes: each arthritic (red and swollen) toe = 1 point<br>Final score = E arthritic toes / 2 (0-5)<br>Ankles 1. slight redness, 2: moderate swelling, 3: severe swelling; 4: maximal inflammation (final score: 0-8) |
| | Final arthritis score = 0-25 |

Treatment:

C4BPd3 group: 50 μg of C4BP(β−) were subcutaneously injected to animals on days 3 and 5. Volume: 0.150 mL.

Reference compound treatments and CAIA control groups (days 5-11):

Enbrel®: 30 mg/kg of Enbrel® was subcutaneously administered to Enbrel group from days 5 to 11. Volume: 5 mL/kg.

Dexamethasone: 1 mg/kg dexamethasone was orally administered to dexamethasone group from days 5 to 11. Volume: 10 mL/kg.

CAIA control group: 0.150 mL of DPBS was subcutaneously administered from days 5 to 11.

Arthritis Monitoring:

Body weights were registered daily from days 0-12 in C4BPd3 and from days 5-12 in CAIA control, dexamethasone and Enbrel® groups. Arthritis scores were determined by the same observer in order to avoid observer bias.

Study End:

The study was finished at day 12.

Animals were anesthetized with isoflurane. Ankles and wrists thickness were measured using a dial thickness gauge. Serum samples were collected and stored at −20° C. Left forelimbs and hindlimbs were dissected and placed in 10% formalin and right forelimbs and hindlimbs were frozen in liquid nitrogen and stored at −80° C.

Spleens were weighted and sectioned in 2 transversal fragments. One of the sections was frozen in liquid nitrogen and stored at −80 C and the other in 10% formalin.

Data Processing and Statistical Analysis:

Data were tabulated, expressed as Mean±SEM, and analysed by using the appropriate statistical test. Significance for all tests was set at $p \leq 0.05$. The statistical analysis was performed using Graph Pad Prism version 5.0.

Arthritis score data were analyzed using a 2-way ANOVA, followed by Bonferroni's posttest. Areas under the dosing curves (AUC) were also determined and analyzed using a one-way analysis of variance (1-way ANOVA), followed by Bonferroni's post-test.

Percentage inhibitions relative to Control Group were calculated.

$$\text{Percentage Inhibition} = 100 - (B/A \times 100)$$

A=Mean Vehicle Control

B=Mean Treated

Ankle and wrist thickness, spleen/body weight ratios were analyzed using a one-way analysis of variance (1-way ANOVA), followed by Bonferroni's post-test.

Body weights data were analyzed using a two-way analysis of variance from day 5 (2-way ANOVA), followed by Bonferroni's post-test.

Results

Intravenous administration of 2 mg anti-CII mAb cocktail followed by 70 µg LPS caused signs of arthritis in 93% of the challenged animals (3 animals with no signs of arthritis were excluded from the study at day 5). Onset disease was reached at days 4-5.

Figure 7:
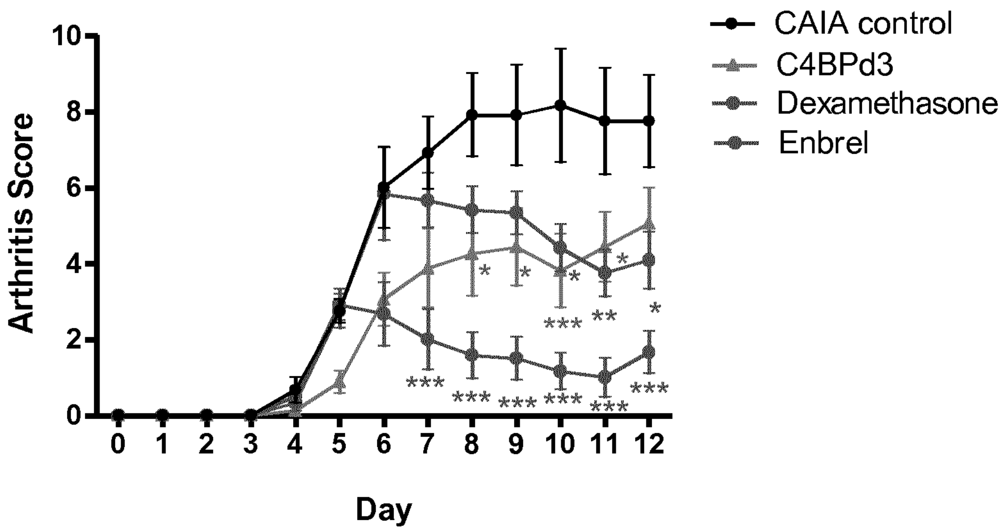
FIG. 7. Arthritic score. CAIA control, C4BPd3 (50 μg of C4BP(β−) at days 3 and 5, sc.), dexamethasone (1 mg/kg at days 5-11, po.), and Enbrel (30 mg/kg at days 5-11 sc.) groups in the CAIA model in mice. Results are expressed as mean±SEM (n=6−8). *$p<0.05$, $p<0.01$, *$p<0.001$ vs. CAIA control group (2-way ANOVA). *$p<0.05$ vs. control group (1-way ANOVA).

In CAIA control group, the severity of the disease increased progressively up to peak disease (day 10). FIG. 7 show arthritis scores evolution in the different experimental groups. FIG. 7 shows that a dose of 50 µg of C4BP(β−) subcutaneously administered at days 3 and 5 confers protection at least until day 12 after the arthritis induction. The group C4BPd3, subcutaneously administered with 50 µg of C4BP(β−) at days 3 and 5 (synchronization and onset arthritis, respectively), significantly ameliorated the progression of arthritis and presented lower arthritis scores during the peak of the disease (8 to 11 days) as compared to CAIA control group (47% inhibition vs. CAIA controls AUC, respectively). Ankle thickness measured at day 12 was significantly lower as compared to CAIA control group (2.74±0.08 mm vs. 3.01±0.08 mm CAIA control, $p<0.05$). No changes in wrist thickness vs. CAIA control were found.

Reference compound dexamethasone (1 mg/kg at days 5-11, po) was highly effective in the murine CAIA model and significantly reduced clinical signs of arthritis from day 7 to 12 (73% inhibition vs. CAIA controls AUC, $p<0.05$). Ankle thickness was significantly lower as compared to CAIA control group (2.63±0.05 mm vs. CAIA control, $p<0.05$). No changes in wrist thickness vs. CAIA control were found.

Enbrel (30 mg/kg at days 5-11, sc) showed progressive reduction of arthritis scores over time and presented significantly lower arthritis scores than CAIA control groups from days 10 to 12 (47% inhibition vs. CAIA controls d12, $p<0.05$). Ankle thickness was significantly lower as compared to CAIA control group (2.73±0.04 mm vs. CAIA control, $p<0.05$). No changes in wrist thickness vs. CAIA control were found.

No remarkable differences between treatment groups (C4BPd3, dexamethasone and Enbrel®) and CAIA control group were found. After LPS injection (day 3) moderate body weight loss (5-10%) was observed although the animals recovered their weight gradually).

Spleen/BW ratio were similar between CAIA control (5.77±0.42 mg/g) and C4BPd3 (5.10±0.17 mg/g) and Enbrel groups (5.13±0.15 mg/g). Dexamethasone induced a significant reduction of spleen/BW ratio vs. CAIA control (3.00±H0.1 mg/g, $p<0.001$).

The results of this study suggest that C4BP (β−) administered in the first phases of CAIA (synchronization) would be effective to stop the progression of arthritis.

The invention claimed is:

1. A method for the treatment of an immunological disease caused by an undesired activation of the immune system by increasing tolerogenic dendritic cell and/or regulatory T cell populations in a subject in need thereof comprising administering to said subject:

a C4BP isoform lacking the beta chain wherein if at least one of the alpha-chains forming said isoform is a deletion mutant which lacks at least one of the complement control protein (CCP) domains, a complement control protein 6 (CCP6) domain is preserved in said alpha-chain; and wherein said C4BP isoform is:

(i) administered subcutaneously in a regimen comprising a plurality of administrations and wherein the C4BP isoform is administered no more than once a week; or (ii) administered subcutaneously at a dose of from 0.24 $mg/m^2$ to 9.99 $mg/m^2$.

2. The method according to claim 1, wherein the dose of each administration in the regimen ranges from 0.24 $mg/m^2$ to 9.99 $mg/m^2$.

3. The method according to claim 1, wherein the C4BP isoform is administered once every two weeks.

4. The method according to claim 1, wherein the C4BP isoform is administered once a week.

5. The method according to claim 1, further comprising a previous step of subcutaneous administration of the C4BP isoform separated by less than seven days from the subsequent administration.

6. The method according to claim 1, wherein the immunological disease is an autoimmune disease selected from the group consisting of systemic lupus erythematosus, lupus nephritis, and rheumatoid arthritis.

7. The method according to claim 6, wherein the autoimmune disease is rheumatoid arthritis.

8. The method according to claim 1, wherein the C4BP isoform lacking the beta chain is selected from the group consisting of $\alpha_7\beta_0$, $\alpha_6\beta_0$ and combinations thereof.

9. The method according to claim 1, wherein the C4BP isoform lacking the beta chain comprises at least one C4BP alpha-chain which is a deletion mutant lacking domains CCP1, CCP2, CCP3 and CCP4.

10. The method according to claim 1, wherein the C4BP isoform comprises the C4BP alpha-chain, wherein the C4BP alpha-chain is a variant in which:

the C4BP alpha-chain comprises the CCP6 domain and a modified complement control protein 8 (CCP8) domain;

wherein the modified CCP8 domain is obtained by modifying an original CCP8 domain having Lys residues; and wherein the original CCP8 is modified by replacing at least one of the Lys residues in the original CCP8 domain by a residue selected from the group consisting of Pro, Asp, Glu, His, Ile, Ala, Ser, Thr, Val, Gln and Asn.

11. The method according to claim 1, wherein the dose ranges from 4 $mg/m^2$ to 6 $mg/m^2$.

12. The method according to claim 1, wherein the C4BP isoform is administered in combination with one or more therapeutic agents useful in the treatment of an immunological disease caused by an undesired activation of the immune system, wherein said therapeutic agent is selected from the group consisting of cyclosporine A, tacrolimus, methotrexate, thiopurines, anti-TNF agents, infliximab, adalimumab, certolizumab, golimumab, etanercept, rituximab, epratuzumab, belimumab, rapamycin, anti-interferon antibodies, tocilizumab, laquinimod, tabalumab, ofatumumab, ixekizumab, brodalumab, briakinumab, sarilumab, rilonacept, anifrolumab, cyclophosphamide, mycophenolate mofetil, azathioprine, anticalcineurinics, prednisolone, methylprednisolone, vitamin D, vasoactive intestinal peptide, hydroxychloroquine, chloroquine, ocrelizumab, atacicept, abatacept, alemtuzumab, sirukumab, eculizumab and T cell vaccine.

13. The method according to claim 2, wherein the dose of each administration is 4.26 $mg/m^2$.

14. A method for the treatment of an immunological disease caused by an undesired activation of the immune system by increasing tolerogenic dendritic cell and/or regulatory T cell populations in a subject in need thereof comprising administering to said subject of a pharmaceutical composition comprising from 0.45 mg to 18.90 mg of:

a C4BP isoform lacking the beta chain wherein if at least one of the alpha-chains forming said isoform is a deletion mutant which lacks at least one of the complement control protein (CCP) domains, the complement control protein 6 (CCP6) domain is preserved in said alpha-chain; and wherein the pharmaceutical composition is administered subcutaneously.

15. The method according to claim 14, wherein the pharmaceutical composition comprises 8.05 mg of the C4BP isoform.

* * * * *

SEQUENCE LISTING

```
<160> NUMBER OF SEQ ID NOS: 5

<210> SEQ ID NO 1
<211> LENGTH: 62
<212> TYPE: PRT
<213> ORGANISM: Homo sapiens

<400> SEQUENCE: 1

Leu Cys Cys Pro Glu Pro Lys Leu Asn Asn Gly Glu Ile Thr Gln His
1               5                   10                  15

Arg Lys Cys Arg Pro Ala Asn His Cys Val Tyr Phe Tyr Gly Asp Glu
            20                  25                  30

Ile Ser Phe Ser Cys His Glu Thr Cys Arg Phe Ser Ala Ile Cys Gln
        35                  40                  45

Gly Asp Gly Thr Trp Ser Pro Arg Thr Pro Ser Cys Gly Asp
    50                  55                  60


<210> SEQ ID NO 2
<211> LENGTH: 30
<212> TYPE: PRT
<213> ORGANISM: Artificial Sequence
<220> FEATURE:
<223> OTHER INFORMATION: Peptide derived from CCP6 domain of C4BP
      alpha-chain

<400> SEQUENCE: 2
```

-continued

```
Leu Ser Ser Pro Glu Pro Lys Leu Asn Asn Gly Glu Ile Thr Gln His
1               5                   10                  15

Arg Lys Ser Arg Pro Ala Asn His Ser Val Tyr Phe Tyr Gly
            20                  25                  30


<210> SEQ ID NO 3
<211> LENGTH: 30
<212> TYPE: PRT
<213> ORGANISM: Artificial Sequence
<220> FEATURE:
<223> OTHER INFORMATION: Peptide derived from CCP6 domain of C4BP
      alpha-chain

<400> SEQUENCE: 3

His Arg Lys Ser Arg Pro Ala Asn His Ser Val Tyr Phe Tyr Gly Asp
1               5                   10                  15

Glu Ile Ser Phe Ser Ser His Glu Thr Ser Arg Phe Ser Ala
            20                  25                  30


<210> SEQ ID NO 4
<211> LENGTH: 30
<212> TYPE: PRT
<213> ORGANISM: Artificial Sequence
<220> FEATURE:
<223> OTHER INFORMATION: Peptide derived from CCP6 domain of C4BP
      alpha-chain

<400> SEQUENCE: 4

Glu Ile Ser Phe Ser Ser His Glu Thr Ser Arg Phe Ser Ala Ile Ser
1               5                   10                  15

Gln Gly Asp Gly Thr Trp Ser Pro Arg Thr Pro Ser Ser Gly
            20                  25                  30


<210> SEQ ID NO 5
<211> LENGTH: 14
<212> TYPE: PRT
<213> ORGANISM: Artificial Sequence
<220> FEATURE:
<223> OTHER INFORMATION: Peptide derived from CCP6 domain of C4BP
      alpha-chain

<400> SEQUENCE: 5

Ile Thr Gln His Arg Lys Ser Arg Pro Ala Asn His Ser Val
1               5                   10
```